US008956284B2

(12) United States Patent
Gorek et al.

(10) Patent No.: US 8,956,284 B2
(45) Date of Patent: Feb. 17, 2015

(54) MINIMALLY INVASIVE RETRACTOR AND POSTED SCREW

(75) Inventors: Josef Gorek, Ross, CA (US); Richard W. Woods, Catonsville, MD (US)

(73) Assignee: K2M, Inc., Leesburg, VA (US)

( * ) Notice: Subject to any disclaimer, the term of this patent is extended or adjusted under 35 U.S.C. 154(b) by 406 days.

(21) Appl. No.: 13/010,301

(22) Filed: Jan. 20, 2011

(65) Prior Publication Data
US 2012/0190934 A1 Jul. 26, 2012

(51) Int. Cl.
*A61B 1/32* (2006.01)

(52) U.S. Cl.
CPC .......................... *A61B 1/32* (2013.01)
USPC ............................ 600/210; 600/201; 600/206

(58) Field of Classification Search
None
See application file for complete search history.

(56) References Cited

U.S. PATENT DOCUMENTS

| | | | |
|---|---|---|---|
| 2,696,817 A | 12/1954 | Prevo | |
| 3,129,706 A | 4/1964 | Reynolds | |
| 4,611,580 A | 9/1986 | Wu | |
| 4,987,892 A | 1/1991 | Krag et al. | |
| 5,242,443 A | 9/1993 | Kambin | |
| 5,505,731 A | 4/1996 | Tornier | |
| 5,582,577 A | 12/1996 | Lund | |
| 5,685,826 A | 11/1997 | Bonutti | |
| 5,902,231 A | 5/1999 | Foley et al. | |
| 5,944,658 A | 8/1999 | Koros et al. | |
| 6,099,547 A | 8/2000 | Gellman et al. | |
| 6,187,000 B1 | 2/2001 | Davison et al. | |
| 6,200,322 B1 | 3/2001 | Branch et al. | |
| 6,206,826 B1 | 3/2001 | Mathews et al. | |
| 6,270,501 B1 | 8/2001 | Freiberg et al. | |
| 6,360,750 B1 | 3/2002 | Gerber et al. | |
| 6,530,926 B1 | 3/2003 | Davison | |
| 6,530,929 B1 | 3/2003 | Justis et al. | |
| 6,537,276 B2 | 3/2003 | Metz-Stavenhagen | |
| 6,616,605 B2 | 9/2003 | Wright | |
| 6,659,945 B2 | 12/2003 | Ball et al. | |
| 6,743,206 B1 | 6/2004 | Smith | |
| 6,796,422 B1 | 9/2004 | Lu | |
| 6,800,084 B2 | 10/2004 | Davison et al. | |
| 6,849,064 B2 | 2/2005 | Hamada | |
| 6,929,606 B2 | 8/2005 | Ritland | |
| 7,008,422 B2 | 3/2006 | Foley et al. | |
| 7,011,660 B2 | 3/2006 | Sherman et al. | |
| 7,056,321 B2 | 6/2006 | Pagliuca et al. | |
| 7,083,621 B2 | 8/2006 | Shaolian et al. | |
| 7,108,705 B2 | 9/2006 | Davison et al. | |
| 7,144,393 B2 | 12/2006 | DiPoto et al. | |
| 7,160,300 B2 | 1/2007 | Jackson | |
| 7,166,107 B2 | 1/2007 | Anderson | |
| 7,179,261 B2 | 2/2007 | Sievol et al. | |

(Continued)

FOREIGN PATENT DOCUMENTS

WO WO 2006/105935 10/2006

*Primary Examiner* — Jerry Cumberledge
*Assistant Examiner* — Nicholas Plionis
(74) *Attorney, Agent, or Firm* — Carter DeLuca Farrell & Schmidt, LLP

(57) ABSTRACT

A minimally invasive retractor assembly includes a posted screw and one or more retractor blades. Each retractor blade is releasably coupled to the posted screw. The retractor blade or blades are manipulated or flexed relative to the posted screw allowing retraction of tissue surrounding the incision. The retractor is made of a biocompatible material, sterile packaged and disposable after one use. A system and method for using the retractor and performing a minimally invasive spine surgical procedure are also disclosed.

13 Claims, 20 Drawing Sheets

(56) References Cited

U.S. PATENT DOCUMENTS

| | | |
|---|---|---|
| 7,188,626 B2 | 3/2007 | Foley et al. |
| 7,250,052 B2 | 7/2007 | Landry et al. |
| 7,261,688 B2 | 8/2007 | Smith et al. |
| 7,491,208 B2 | 2/2009 | Pond, Jr. et al. |
| 7,625,379 B2 | 12/2009 | Puno et al. |
| 7,666,189 B2 | 2/2010 | Gerber et al. |
| 7,846,093 B2 | 12/2010 | Gorek et al. |
| 2005/0065517 A1 | 3/2005 | Chin |
| 2006/0229614 A1 | 10/2006 | Foley et al. |
| 2006/0264962 A1 | 11/2006 | Chin et al. |
| 2007/0055247 A1 | 3/2007 | Jahng |
| 2007/0129731 A1 | 6/2007 | Sicvol et al. |
| 2007/0167954 A1 | 7/2007 | Sicvol et al. |
| 2008/0161650 A1* | 7/2008 | Hestad et al. .............. 600/245 |
| 2008/0262318 A1* | 10/2008 | Gorek et al. .............. 600/235 |
| 2009/0222046 A1* | 9/2009 | Gorek .............. 606/279 |

\* cited by examiner

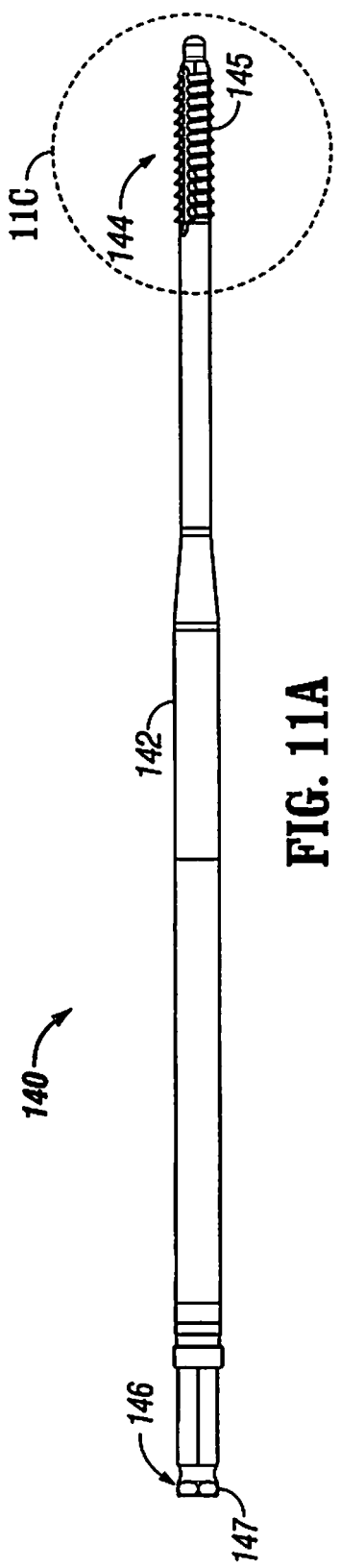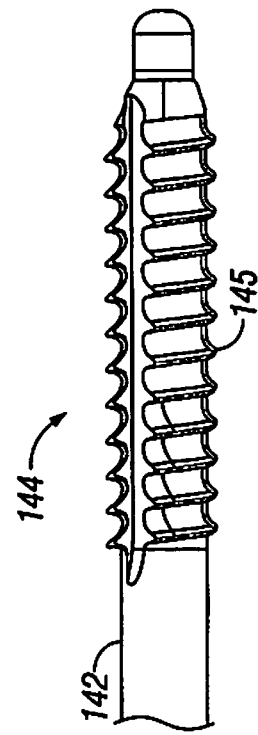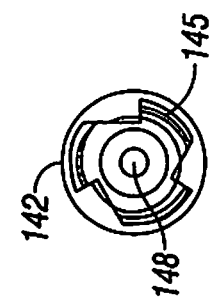
FIG. 11A
FIG. 11C
FIG. 11B

MINIMALLY INVASIVE RETRACTOR AND POSTED SCREW

BACKGROUND

1. Technical Field

This invention relates generally to orthopedic spine surgery and in particular to a minimally invasive retractor with a posted screw and methods for use in a minimally invasive surgical procedure.

2. Description of Related Art

There has been considerable development of retractors and retractor systems that are adapted for use in less invasive procedures. Many of the recent developments are based on traditional types of surgical retractors for open procedures, predominantly table-mounted devices of various designs. These devices tend to be cumbersome and are not well adapted for use in small incisions. Standard hand-held surgical retractors are well known and can be modified to fit the contours of these small incisions, but they require manual manipulation to maintain a desired placement, thereby occupying one hand of the physician or requiring another person to assist the physician during the procedure. Typical retractors are also positioned into the soil tissue and are levered back to hold the wound open, frequently requiring re-positioning if they dislodge, obstruct the physician's view, or interfere with access to the surgical site.

In recent years, minimally invasive surgical approaches have been applied to orthopedic surgery and more recently to spine surgery, such as instrumented fusions involving one or more vertebral bodies. Unlike minimally invasive procedures such as arthroscopic knee surgery or gallbladder surgery where the affected area is contained within a small region of the body, spinal fusion surgery typically encompasses a considerably larger region of the patient's body. In addition, arthroscopic surgery and laparoscopic surgery permit the introduction of fluid (i.e., liquid or gas) for distending tissue and creating working space for the surgeon. Surgery on the spine does not involve a capsule or space that can be so distended, but instead involves multiple layers of soft tissue, bone, ligaments, and nerves. For these reasons, the idea of performing a minimally invasive procedure on the spine has only recently been approached.

By way of example, in a typical spine fusion at least two vertebral bodies are rigidly connected using screws implanted into the respective vertebral bodies with a solid metal rod spanning the distance between the screws. This procedure is not generally conducive to a minimally invasive approach. The insertion of pedicle or facet screws is relatively straightforward and can be accomplished through a minimal incision. For example, difficulty arises upon the introduction of a length of rod into a very small incision with extremely limited access and visibility. A single level fusion may require a 30-40 mm rod to be introduced into a 1 cm incision and a multilevel fusion may require a rod several inches long to fit into a 1 cm incision. For this reason, it is important that the minimal incision be maintained in an open and accessible condition (i.e., as wide as practicable) for introduction of the rod.

Minimally invasive surgery offers significant advantages over conventional open surgery. First, the skin incision and subsequent scar are significantly smaller. By using more than one small incision rather than one large incision, the need for extensive tissue and muscle retraction may be greatly reduced. This leads to significantly less vascular and muscular damage, less blood loss, reduced post-operative pain, a shorter hospital stay, and a faster overall recovery.

Most spine implant procedures are open procedures, and while many manufacturers advertise a minimally invasive method, the procedure is typically not recommended for fusions and focus on more common and accepted minimally invasive spine procedures such as kyphoplasty, vertebroplasty, and discectomy.

Medtronic Sofamor Danek's SEXTANT® is a true minimally invasive device used for screw and rod insertion. Its shortcomings lie with how complicated the system is to use and the requirement for an additional incision for rod introduction. This system also requires that the guidance devices be rigidly fixed to the pedicle screw head in order to maintain instrument alignment and to prevent cross-threading of the setscrew. For these reasons, the surgeon cannot access the surrounding anatomy for complete preparation of the field. Nor does SEXTANT® allow for any variation in the procedure, if need be.

Depuy Spine's VIPER™ system is another minimally invasive implant and technique recommended for one or two level spine fusions. This system is less complicated than the SEXTANT® only requiring two incisions for a unilateral, one-level fusion, but it is limited in the same way as the SEXTANT® because it also requires the instrumentation to be rigidly fixed to the pedicle screw.

Spinal Concept's PATHFINDER® and NuVasive's SPHERX® spinal system (as disclosed in U.S. Pat. No. 6,802,844), are marketed as "minimally disruptive" spine fusion implants and procedures. While they have advantages over a general "open" procedure, they do not provide all of the advantages of a truly minimally invasive approach. Their characterization as "minimally open" procedures is a result of the inherent difficulty of introducing a rod in a minimally invasive spinal procedure. In order to introduce a rod long enough to accomplish a single level fusion, these systems describe an incision long enough to accept such a rod, thereby undermining the advantages of a minimally invasive approach.

The problem of rod introduction warrants further discussion as it is the central problem in minimally invasive spinal fusions. The systems currently on the market address this issue by adding another incision, using a larger incision, or avoiding the issue completely for fusions greater than one level.

In order to be truly minimally invasive, a spine fusion procedure should have a minimum number of small incisions and not require significant tissue and/or muscle retraction. Furthermore, an improved approach should encompass as many variations and applications as possible thereby allowing the surgeon to adjust the procedure to accommodate the anatomy and surgical needs of the patient as presented. For instance, spinal fusions should not be limited to just one or two levels.

Therefore, a continuing need exists for an improved device, an improved system, and an improved method for performing minimally invasive spine surgery.

SUMMARY

Disclosed herein is a minimally invasive retractor assembly including a retractor including one or more retractor blades, and a posted screw. The screw includes a post and a shank. The shank of the screw is insertable into bone, e.g., a vertebral body. The screw may include a channel (cannula) extending longitudinally through the length of the screw. In an embodiment, the channel may extend fully through the length of the screw. However, in other embodiments, the channel may extend partially through the length of the screw.

The one or more retractor blades of the retractor are releasably coupled to the screw, and are flexible relative to the screw. In embodiments, the retractor assembly may include additional retractors that are releasably coupled to the same screw as the first retractor. Each additional retractor includes one or more retractor blades. The one or more retractor blades are radially movable, i.e., flexible, relative to the longitudinal axis of the screw.

The post of the screw is receivable within an aperture of the first retractor. The screw may include a shank and a transition member positioned between the post and the shank of the screw. The transition member may include a generally cylindrical portion and a tapered portion. The tapered portion of the transition member may taper proximally toward the post. A collar may be positioned between the shank and the transition member.

In the embodiments that are described herein, the retractor blades are releasably coupled to the screw in different ways. For example, the first retractor may include an aperture at its distal end for receiving the post of the screw. In an embodiment, the one or more retractor blades and the transition member may have complementary members, e.g., protrusions and recesses, that engage one another to releasably secure the one or more retractor blades to the transition member of the screw. The distal sections of the one or more retractor blades may be substantially parallel to one another. In other embodiments, the distal sections of the one or more retractor blades may curve inwardly or may have another configuration, i.e., shape, which corresponds to the configuration of the transition member. The complementary configurations of the transition member and the one or more retractor blades facilitate releasably securing the screw and the one or more retractor blades. Moreover, one or more protrusions may extend from an outer surface of the transition member. The one or more protrusions are receivable within one or more grooves or lumens within the one or more retractor blades.

The protrusions may extend, for example, proximally or orthogonally, from the screw (for example, from the collar or the transition member of the screw) that is received within the one or more lumens of the one or more retractor blades. In an embodiment, the collar and/or the transition member of the screw may include lumens that receive protrusions extending from the one or more retractor blades.

A locking mechanism for releasably coupling the retractor blades to the screw is also disclosed. In particular, the minimally invasive retractor assembly may also include a channel that extends from a proximal end of the post. In addition, a pin that is coupled to a wire is receivable through the channel. The pin may serve as a locking mechanism to releasably secure the retractor blades to the screw. In particular, the retractor blades may include protrusions (or fingers) that extend substantially orthogonally from the retractor blades and are received within lumens extending substantially orthogonally through a transition member, between the post and the shank, and intersecting the channel. After placement of the protrusions (or fingers) of the retractor blades, the pin may be placed through the channel and through openings within the protrusions (or fingers), thereby securing the retractor blades to the screw. Releasing of the retractor blades from the screw is achievable by proximally translating the wire to which the pin is attached, thereby unlocking the retractor blades from the transition member.

In an embodiment, a posted screw may include a transition member that defines an arcuate, e.g., substantially parabolic configuration, corresponding to the shape of the retractor. The screw may be seated within the retractor and the corresponding shape of the screw and retractor facilitates the reliable securing of the screw within the retractor. Protrusions and/or grooves or lumens on the retractor blades and the screw facilitate further securing of the screw and the retractor blades to one another. In an embodiment, the retractor blade may be overmolded onto the screw, e.g., onto the transition member of the screw.

Also disclosed herein is a method for performing a surgical procedure. In particular, a minimally invasive retractor assembly including at least one retractor is provided. The at least one retractor includes one or more retractor blades and a screw including a post. The one or more retractor blades are releasably coupled to the screw, and are configured and adapted to be radially translatable, e.g., flexible, relative to the longitudinal axis of the screw. The screw is threaded into bone of the patient, and the one or more retractor blades are radially translated relative to the longitudinal axis of the screw to facilitate retraction of skin and tissue adjacent to the one or more retractor blades. Once the desired surgical procedure is performed, the at least one retractor may be separated from the retractor assembly. For example, the continued radial translation (beyond a given range of motion) of the one or more retractor blades relative to the longitudinal axis of the screw may result in the separation of the retractor from the screw.

These and other embodiments of the present disclosure will be described in greater detail below with reference to the accompanying figures.

BRIEF DESCRIPTION OF THE DRAWINGS

Embodiments of the presently disclosed minimally invasive retractor and posted screw are described herein with reference to the accompanying drawings, wherein:

FIG. 11A is a side view of a cannulated bone screw tap;

FIG. 11B is a front elevational view of the bone screw tap of FIG. 11A;

FIG. 11C is an enlarged side view of the indicated area of detail of FIG. 11A;

DETAILED DESCRIPTION OF THE EMBODIMENTS

Figure 4:
FIG. 4 is a bottom view of the minimally invasive retractor of FIG. 3.

Embodiments of the presently disclosed minimally invasive retractor and posted screw will now be described in detail with reference to the drawings wherein like reference numerals identify similar or identical elements. In the drawings and in the description which follows, the term "proximal", as is traditional, will refer to the end of the minimally invasive retraction device which is closest to the operator while the term "distal" will refer to the end of the device which is furthest from the operator. Examples of suitable minimally invasive retractors are disclosed in U.S. Pat. No. 7,846,093, the contents of which are hereby incorporated by reference in their entirety.

Figure 2:
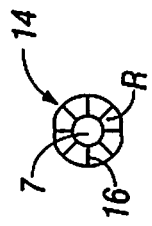
FIG. 2 is a bottom perspective of a minimally invasive retractor of FIG. 1.
Figure 1:
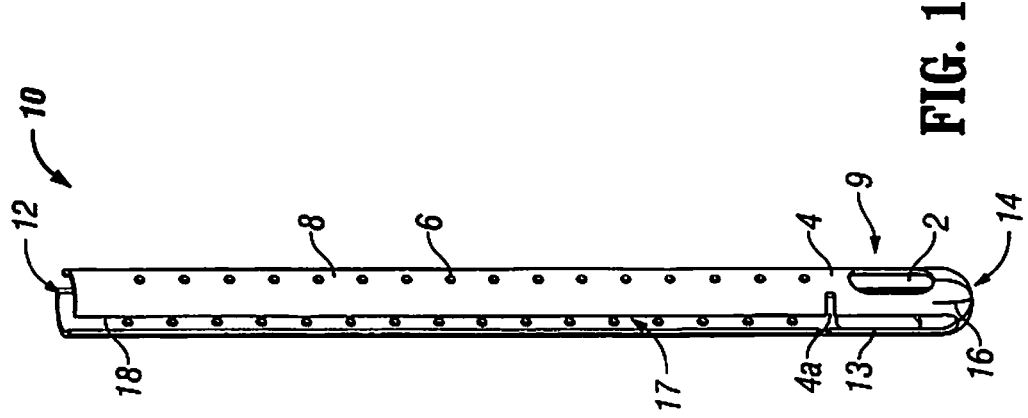
FIG. 1 is a perspective view of a minimally invasive retractor according to a first embodiment of the present disclosure.

Referring initially to FIGS. 1 and 2, a first embodiment of the presently disclosed minimally invasive retractor is illustrated and generally designated as 10. Retractor 10 includes an open proximal end 12 and a distal end 14. In addition, retractor 10 includes a pair of retractor blades 8 having a plurality of instrument holes 6 disposed on each of retractor blades 8. Instrument holes 6 are configured and dimensioned to cooperate with different surgical instruments as will be discussed in detail hereinafter. A distal region 9 of retractor 10 includes an opening 7 (FIG. 2), at least one slot or window 2, and a pair of arms 13 extending from distal end 14 to a flexible region or living hinge 4. Window 2 is sized and configured to receive instruments therethrough. Each retractor blade 8 is attached to living hinge 4 to define a substantially continuous elongate member. A pair of recesses 4a is formed between retractor blade 8 and arm 13 to define living hinge 4.

Distal end 14 optionally may include at least one relief region R (FIG. 2) defined by at least one slit 16 extending proximally from opening 7 (FIG. 2). Alternatively, slit 16 may originate at window 2 and extend distally towards opening 7. It is contemplated that other arrangements of relief structures may be used to define relief region R and these may exist between opening 7 and window 2. Each slit 16 is a weakened portion of distal end 14. It may be a score in the material, a perforated region in the material, or another structural arrangement allowing relief region R to be radially displaced away from the centerline of retractor 10 in response to applied forces as will be discussed in detail hereinafter. In addition, distal end 14 has a generally convex outer surface that facilitates insertion of retractor 10 through layers of body tissue.

Retractor blades 8 and arms 13 are generally arcuate structures that cooperate to define a substantially circular configuration for retractor 10. Each retractor blade 8 and each arm 13 have an arcuate configuration that is less than about 180° and are radially spaced apart to define a continuous slot 17 along a substantial portion of retractor 10. In addition, each retractor blade 8 and its corresponding arm 13 define a passage 18 that also extends substantially the entire length of retractor 10. Passage 18 is expandable, as will be discussed in detail hereinafter, for receiving a rod (not shown) therein. Retractor blades 8 and arms 13 define a substantially circular ring shape, thereby providing sufficient stiffness (i.e., rigidity) such that retractor blades 8 and arms 13 resist bending from the counter forces of the retracted tissues.

Opening 7 is located at distal end 14 of retractor 10 and is sized for receiving the threaded post 30 of a screw 20 (FIG. 16) therethrough, so as to support screw 20 at distal end 14 of retractor 10. In addition, as shown in FIGS. 5-8 and 26-29, the opening 7 may receive the shank of a threaded screw 40 having a head 42 adapted to receive rod 3 in a secured relation. The opening 7 is sized to inhibit passage of head 42 so as to support screw 40 at distal end 14 of the retractor 10.

Retractor 10 is formed from a suitable biocompatible material having the desired physical properties. That is, retractor 10 is formed of a biocompatible, sterilizable material in a suitable configuration and thickness so as to be sufficiently rigid to be held on the screw when desired during insertion and a surgical procedure and to provide retraction of tissue, and yet is sufficiently bendable to be spread apart to provide retraction and to be forcibly removed from the screw as necessary and appropriate. It is contemplated that retractor 10 may be formed from polymers such as polypropylene, polyethylene, or polycarbonate. Additionally, retractor 10 may be formed from silicone, polyetheretherketone ("PEEK"), metal (such as stainless steel, titanium or nitinol) or another suitable material. Retractor blade 8 is bendable away from the centerline of retractor 10 in response to applied forces, wherein retractor blade 8 bends at living hinge 4. Bending retractor blade 8 away from the centerline (i.e., radially outwards) creates a larger opening through retractor 10 and also acts to retract the surrounding tissue at the selected surgical site. Installation and use of retractor 10 in surgical procedures will be discussed in detail hereinafter.

Figure 3:
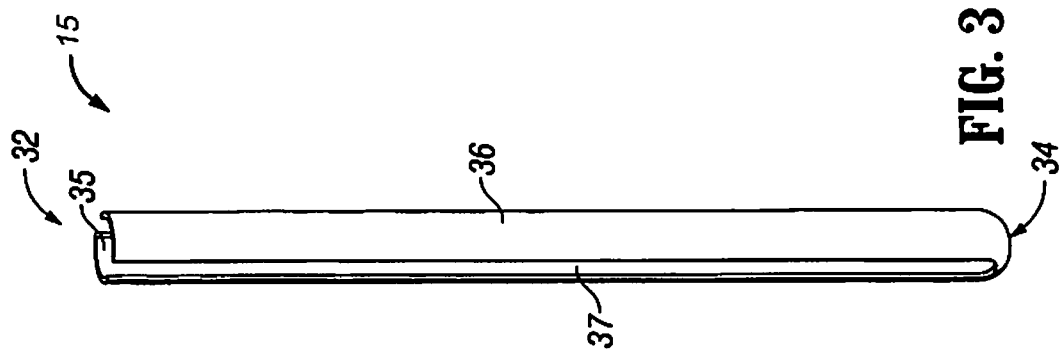
FIG. 3 is a perspective view of a minimally invasive retractor according to a second embodiment of the present disclosure.

Referring now to FIGS. 3 and 4, a second embodiment of the present disclosure is illustrated as retractor 15 having an open proximal end 32 and a distal end 34. Retractor 15 includes a pair of retractor blades 36. Similar to retractor 10, distal end 34 is adapted to mate with a threaded shank of a posted pedicle screw. Additionally, retractor 15 includes an opening 7 (FIG. 4) that is substantially identical to opening 7 of retractor 10. As in the previous embodiment, blades 36 have an arcuate configuration that is less than about 180° and are radially spaced apart to define a continuous slot 37 along a substantial portion of retractor 15.

Furthermore, retractor blades 36 define a passage 35 through retractor 15. In this embodiment, retractor blades 36 are also flexible, but bend radially outwards from a centerline of retractor 15 near relief regions R (FIG. 4). As in the previous embodiment, relief regions R defined by slits 16 (shown as a pair of slits in FIG. 4) as previously discussed in connection with retractor 10 may be provided.

In this embodiment, retraction of tissue with retractor blades 36 utilizes manual manipulation of retractor blades 36 by the physician rather than using a surgical instrument in cooperation with instrument holes 6 of retractor 10 (FIG. 1). If relief regions are provided, removal of retractor 15 from the surgical site may accomplished by pulling retractor 15 proximally (i.e., away from the pedicle screw) and spreading or breaking distal end 34 along slits 16 such that relief regions R and retractor blades 36 separate from each other. As such, the physician can readily remove the two parts from the surgical site. Similar to passage 18 (FIG. 1), passage 36 is selectively expandable and contractible for receiving rod (not shown) therein.

Figure 5:
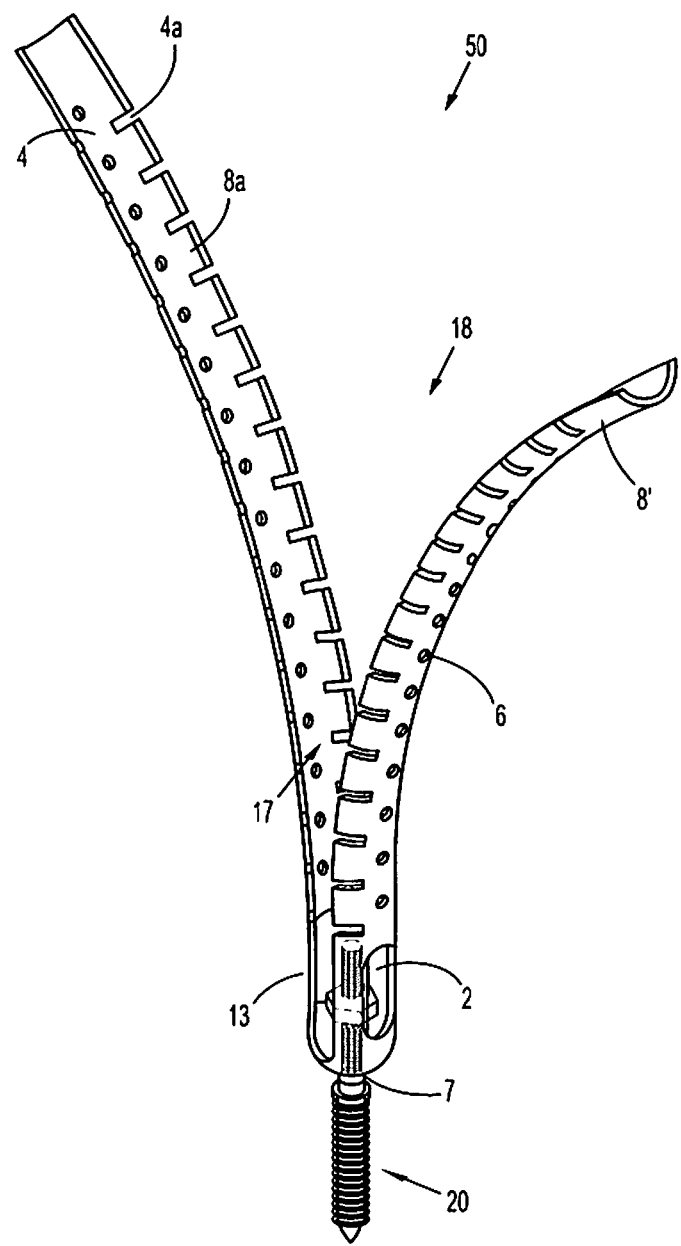
FIG. 5 is a perspective view of a minimally invasive retractor and screw assembly in accordance with a third embodiment of the presently disclosed minimally invasive retractor.

Another embodiment of the presently disclosed retractor is illustrated in FIG. 5 and shown generally as retractor 50. Retractor 50 is similar to retractor 10, and is adapted to receive posted screw 20 within opening 7. Retractor 50 differs from retractor 10 in the following ways that will now be described. In particular, retractor 50 includes a plurality of living hinges 4 along with their respective recesses 4a. Retractor 50 may be about 6 inches long and may be readily adjusted to a desired length by removing excess material by using scissors or a knife. In addition, retractor 50 has an inner diameter that is approximately 16 mm and retractor blades are approximately 1 mm thick. Each living hinge 4 is about 1-2 mm in height and each blade section 8a is about 5 mm. Instrument holes 6 are on 1 cm centerlines. Slot 17 is typically at least 5.5 mm, but will vary according to the size of the rod that will be inserted into the patient. In particular, each retractor blade 8' includes a plurality of blade sections 8a. Each blade section 8a is connected to an adjacent blade section 8a by a living hinge 4. Thus, the plurality of blade sections 8a and living hinges 4 define retractor blade 8'. As described with respect to retractor 10 (FIG. 1), each blade section 8' is substantially parallel to arm 13 to define slot 17 between retractor blades 8'. The retractor blades 8' are transitionable between a first state in which the blades 8' are substantially parallel and a second state in which the blades 8' form a V-shaped configuration (FIG. 5).

Additionally, the plurality of living hinges 4 greatly increases the adaptability of retractor 50 in comparison to retractor 10. While retractor blades 8 of retractor 10 (FIG. 1) generally bend at its single living hinge 4, the additional living hinges 4 present along retractor blades 8' of retractor 50 permit bending with increased flexibility at a number of positions along the length of each retractor blade 8'. Thus, retractor blades 8' will bend at the living hinge 4 that corresponds to the plane defined by the surface of the patient's body tissue.

By using this construction, retractor 50 is usable in patients having different tissue thicknesses between the vertebral body and the surface of their skin. In addition, since each retractor blade 8' has a plurality of living hinges 4 and blade sections 8a, it is not required for each retractor blade 8' to bend at the same point along the length of retractor 50, thereby accommodating variances in the depth that retractor 50 is inserted. For example, one retractor blade 8' may bend at its fourth living hinge 4, while the other retractor blade 8' may bend at its sixth living hinge 4, thereby accommodating variances in tissue thickness and orientation of retractor 50. The retractor blades 8' may define a first state in which the retractor blades 8' are substantially parallel to one another (not shown) and a second state in which the retractor blades define a substantially V-shaped configuration (FIG. 5), as well as intermediate states between the first and second states.

Figure 6:
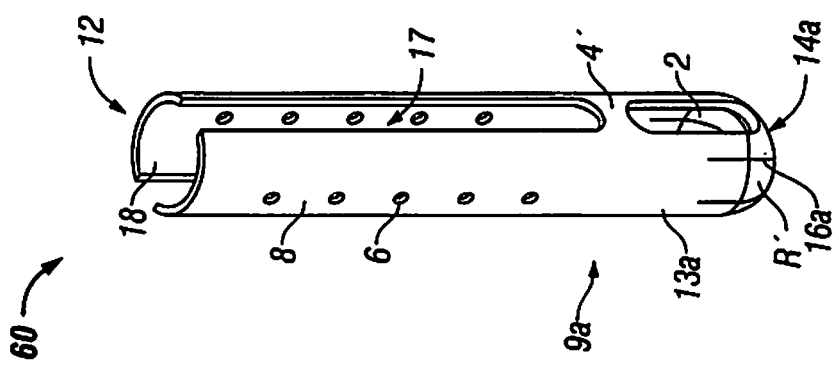
FIG. 6 is a perspective view of a fourth embodiment of the presently disclosed minimally invasive retractor.

In FIG. 6, a further embodiment of the presently disclosed retractor is illustrated and generally referenced as retractor 60. Retractor 60 is similar to retractor 10 (FIG. 1) with the differences discussed in detail hereinafter. As in the previous embodiment, retractor 60 includes a distal end 14a with a distal region 9a. Distal region 9a includes arms 13a that extend circumferentially and do not form a portion of slot 17 as in the previous embodiment. A living hinge 4' is defined between window 2 and slot 17. In addition, distal region 9a optionally may include slits 16a that are full cuts through the material of distal region 9a defining a plurality of relief regions R'. This configuration permits a surgeon to remove and subcutaneously relocate retractor 60 to gain access to the vertebral disc space. As in the previous embodiments, positioning window 2 distally of slot 17 allows retractor 60 to expand in a medial-lateral orientation such that rod (not shown) may be inserted through passage 18 into the target site.

Figure 7:
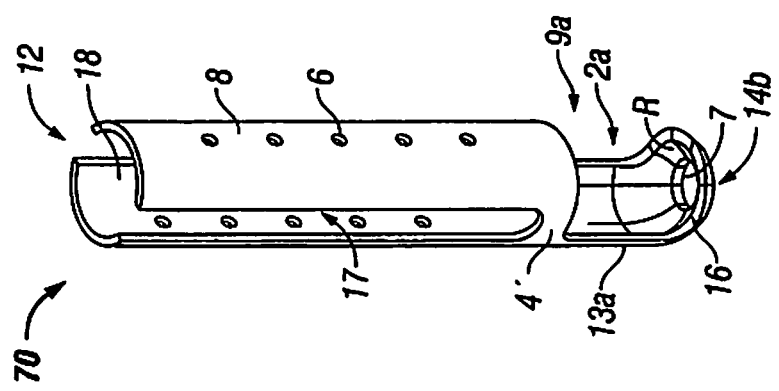
FIG. 7 is a perspective view of a fifth embodiment of the presently disclosed minimally invasive retractor.

FIG. 7 illustrates an alternate embodiment of the presently disclosed retractor that is generally referenced as 70. Retractor-70 is substantially similar to the embodiment previously identified as retractor 60 (FIG. 5). However, in this embodiment distal region 9a only includes one arm 13a, thereby increasing the lateral opening near distal end 14b and defining window 2a that is larger than previously disclosed window 2 (FIG. 5). This embodiment provides increased access to the target site, thereby allowing larger implants or instruments to be positioned in the target site.

Figure 8:
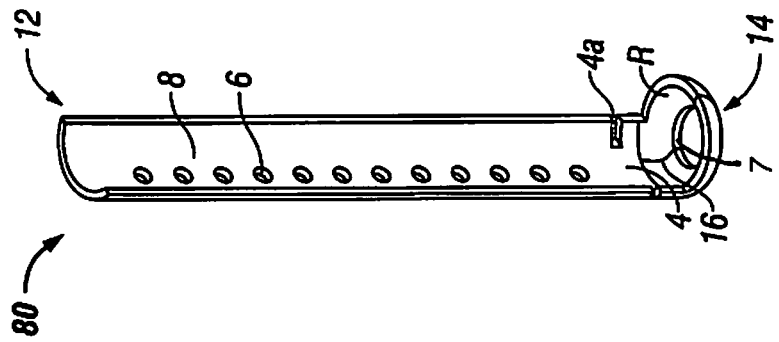
FIG. 8 is a perspective view of a sixth embodiment of the presently disclosed minimally invasive retractor.

Another embodiment of the presently disclosed retractor is illustrated in FIG. 8 and referenced as retractor 80. Retractor 80 includes the same or substantially similar components as described hereinabove with respect to retractor 10 (FIG. 1). In this embodiment, retractor 80 includes only one retractor blade 8. This configuration allows greater variability in creating the retracted space as well as increasing access to the target site for using larger instruments or inserting larger devices than possible with retractor 10 (FIG. 1).

Figure 9:
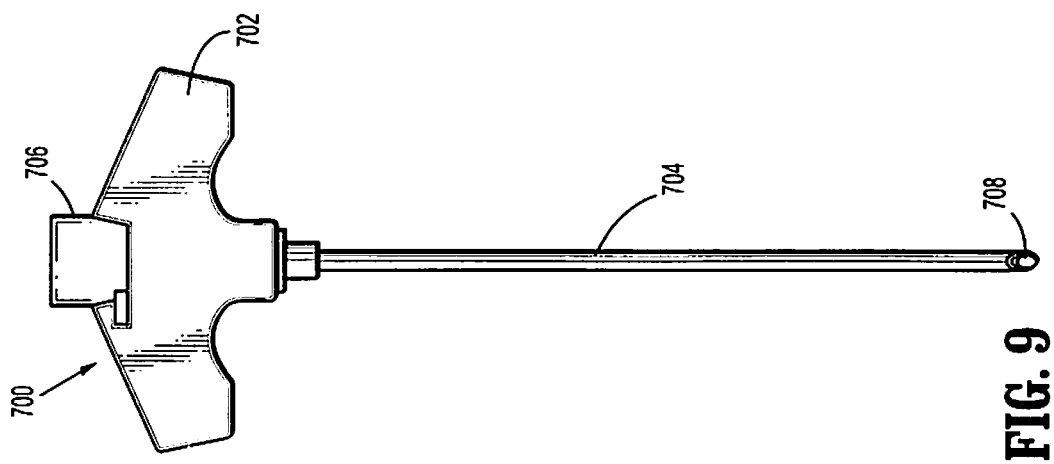
FIG. 9 is a top plan view of a bone biopsy needle.

In FIG. 9, a bone biopsy needle (e.g., a Jamshidi needle) 700 is illustrated. Needle 700 includes a handle 702 disposed at a proximal end of needle 700, an elongate tubular member 704 extending distally from handle 702, and a stylet 706. Stylet 706 has a sharpened distal tip 708 that is adapted for penetrating tissue, including bone. In addition, tubular member 704 has a lumen extending from its proximal end to its distal end for receiving stylet 706 therethrough. Stylet 706 is releasably attached to handle 702 such that it may be removed once the target site has been pierced by distal tip 708.

Figure 10B:
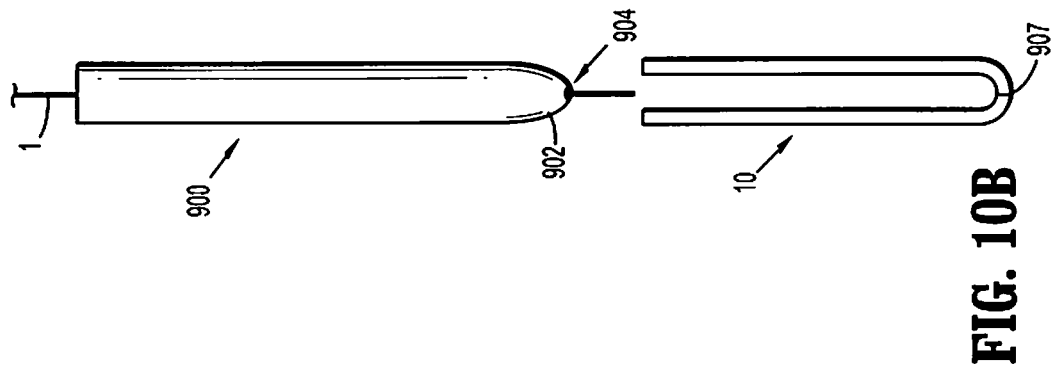
FIG. 10B is a side view of a dilator and the retractor of FIG. 1.
Figure 10A:
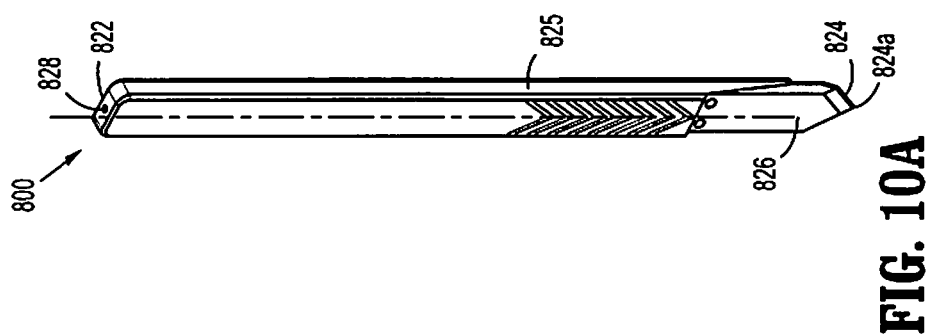
FIG. 10A is a perspective view of a scalpel.

Referring now to FIG. 10A, a cannulated scalpel 800 is illustrated. Scalpel 800 includes a housing 825 having a blade 826 disposed therein. Blade 826 has a sharpened distal end 824 for separating tissue. In addition, distal end 824 includes an opening 824a that cooperates with an opening 828 located at proximal end 822 and defines a channel through scalpel 800 for slidably receiving guidewire 1 (FIG. 10B) therethrough.

FIG. 10B shows a dilator 900 configured and dimensioned to be received through a retractor 10 with distal atraumatic blunt tip 902 protruding through opening 907 in retractor 10. Dilator 900 includes a longitudinal passage therethrough having distal opening 904 for receiving guidewire 1 therethrough. Alternatively, it is contemplated that rather than a retractor, dilator 900 may be used together with a cannula (not shown). In other embodiments, a series of dilators and cannulae may be used.

In FIGS. 11A-C, a cannulated bone tap 140 is shown. Bone tap 140 includes an elongated body 142 having a proximal end 146 and a distal end 144. Distal end 144 includes a helical thread 145 for forming threads in a hole that is formed in a bony structure (i.e. a vertebral body). Proximal end 146 includes a tool engagement region 147 that is adapted for cooperating with a driving or rotating tool (not shown) and forming the threads in the bony structure. Driving and rotating tools are well known in the art. In addition, proximal end 146 and distal end 144 cooperate to define a channel 148 extending through bone tap 140 such that bone tap 140 may be slid along guidewire 1. Bone tap 140 is available in a number of different sizes in a range of about 5.5 mm to about 7.5 mm. Alternatively, other bone taps may be used that match the size of the screw threads of the screw that will be implanted into bone.

Figure 12:
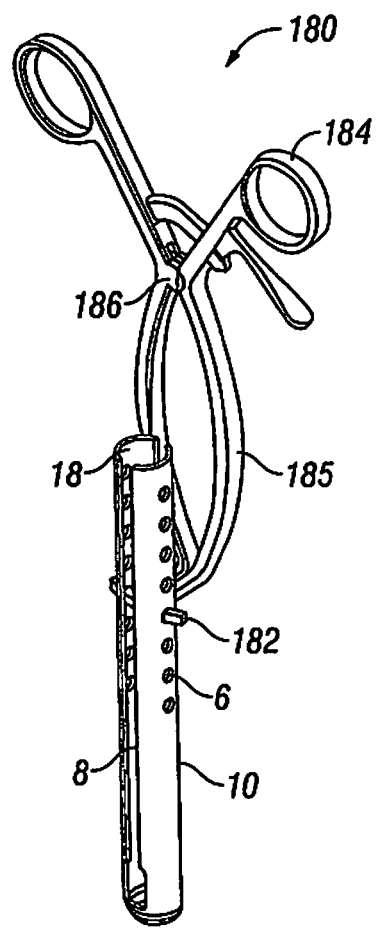
FIG. 12 is perspective view of a retraction assembly having a minimally invasive retractor and a Gelpi retractor.

A common spreader, or Gelpi retractor 180 is shown in FIG. 12 in cooperation with retractor 10. Gelpi retractor 180 includes a pair of arcuate arms 185 that are pivotably connected at pivot point 186. A pair of finger rings 184 are located at a proximal end of Gelpi retractor 180 that permit the physician to selectively move arms 185 towards and away from each other. A finger 182 is located at a distal end of each arm 185 and is configured to releasably engage an instrument hole 6 in retractor 10. As shown, finger rings 184 are laterally offset from arms 185. Thus, pivotable movement of arms 185 urge retractor blades 8 towards and away from each other in response to movement of finger rings 184. The Gelpi retractor 180 facilitates blade movement radially relative to the longitudinal axis of the retractor 10, thereby facilitating retraction of tissue adjacent the blade 8. Moving finger rings 184 towards each other pivots arms 185 away from each other and urge retractor blades 8 away from each other, thereby enlarging passage 18. Consequently, movement of finger rings 184 away from each other has the opposite effect. Gelpi retractor 180 is also configured and adapted to cooperate with retractor 50, 60, and 70.

Figure 13:
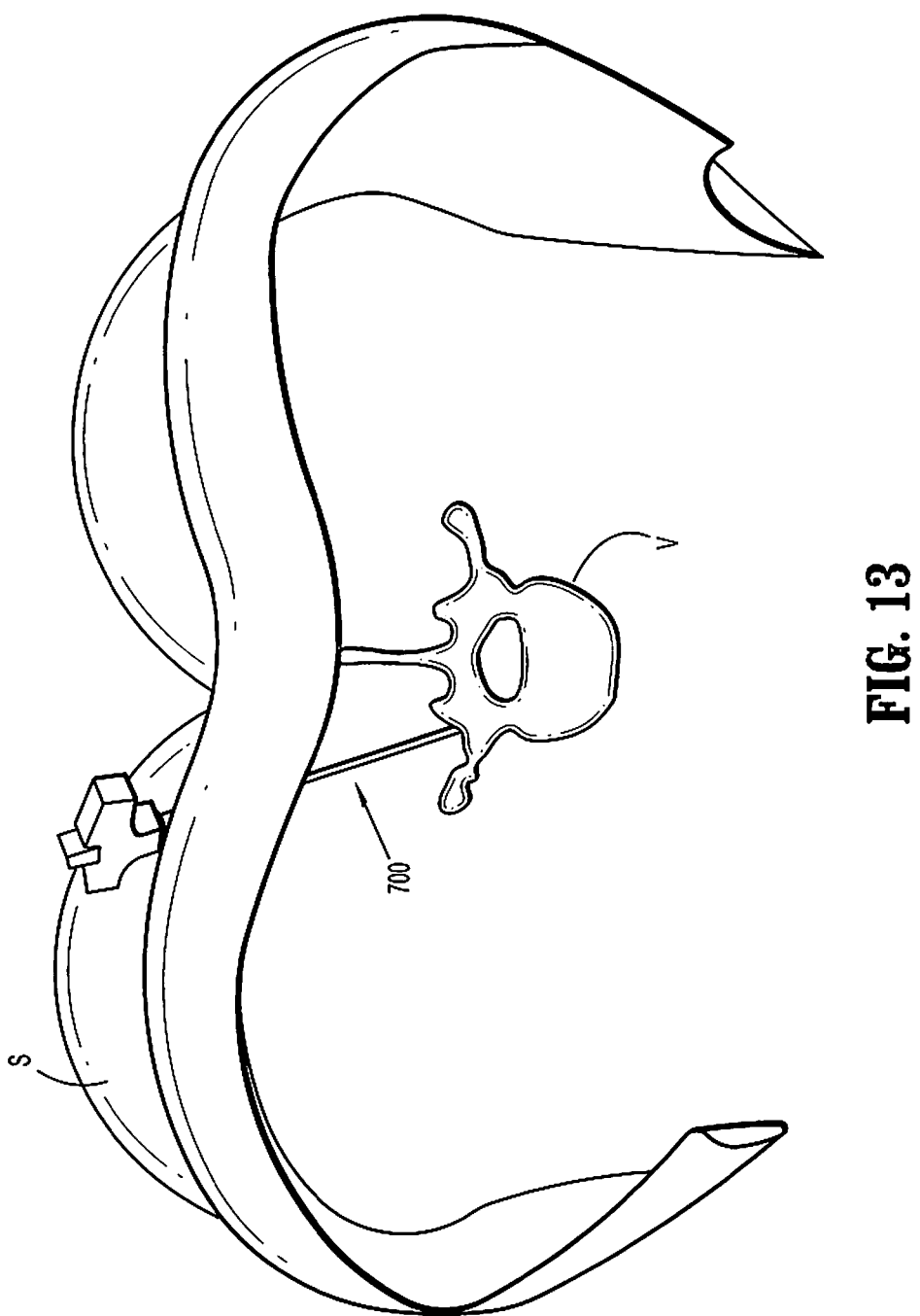
FIG. 13 is a front cross-sectional view of a vertebral body illustrating insertion of the bone biopsy needle of FIG. 9.
Figure 14:
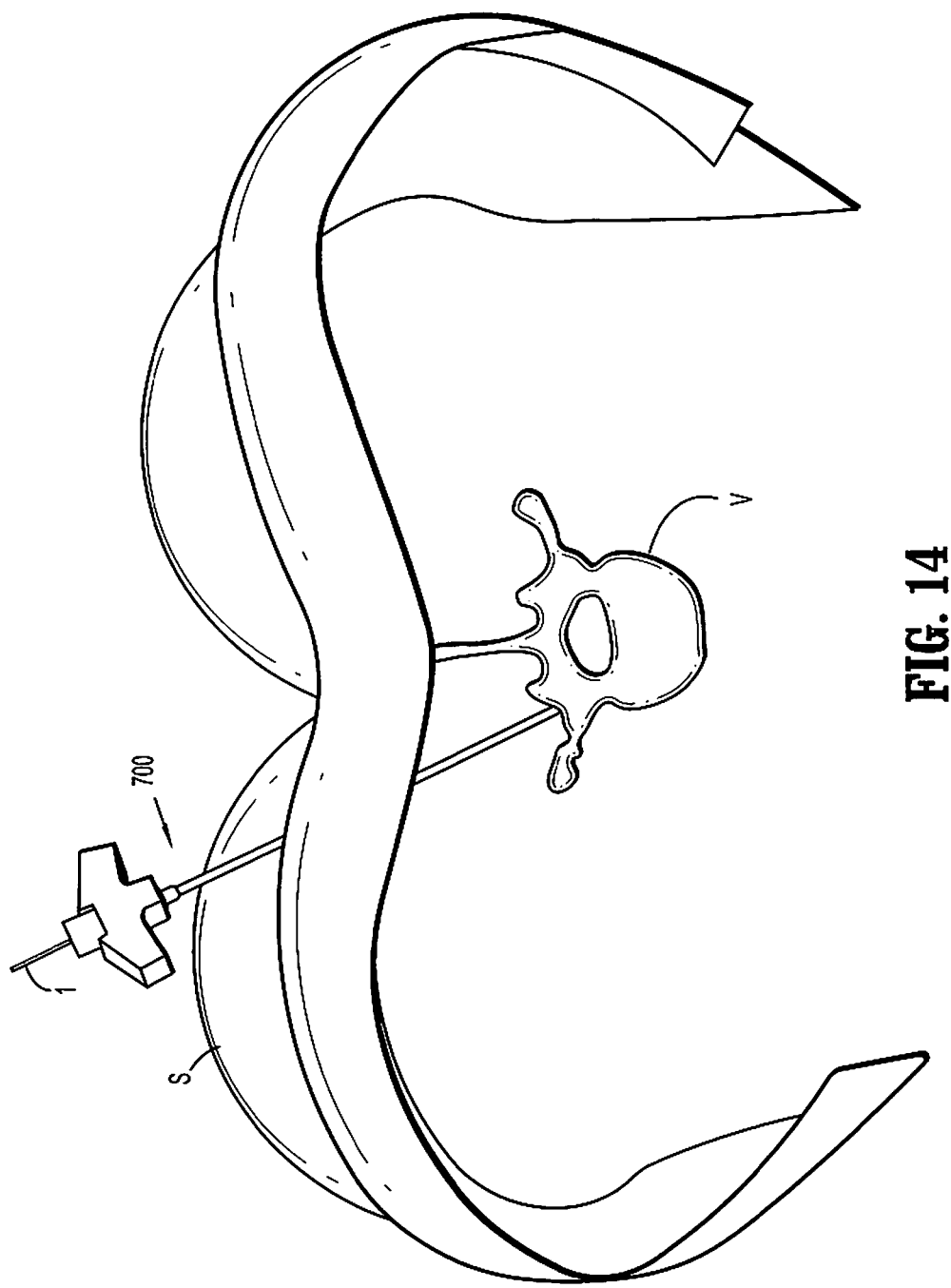
FIG. 14 is a front cross-sectional view of the vertebral body of FIG. 13 illustrating insertion of a guide wire through the bone biopsy needle of FIG. 9.
Figure 15:
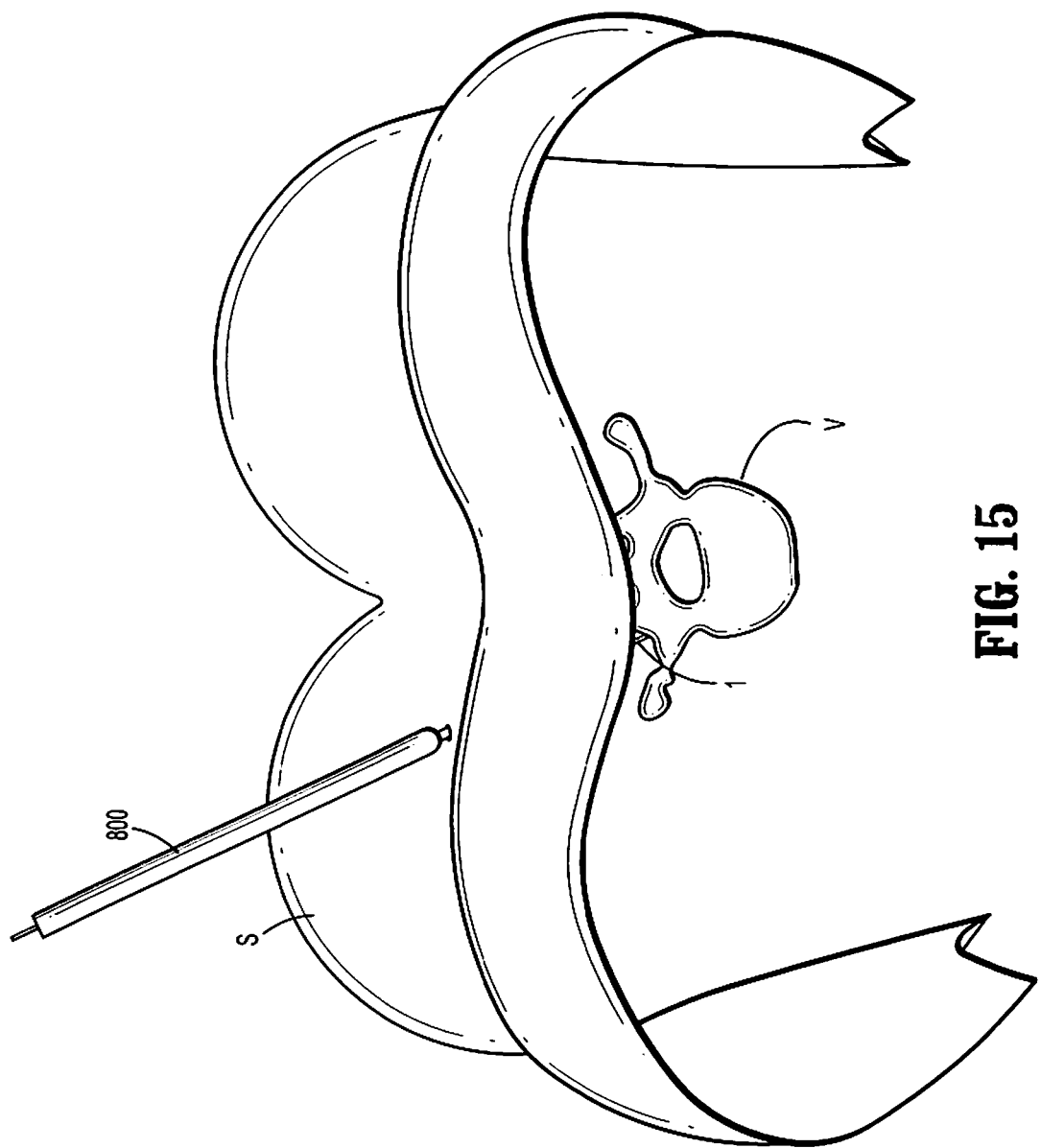
FIG. 15 is a front cross-sectional view of the vertebral body of FIG. 14 illustrating insertion of a guide wire through the scalpel of FIG. 10A.

Use of the biopsy needle 700 and the scalpel 800 will now be described with respect to FIGS. 13-15. The biopsy needle 700 may be inserted through skin S of the patient until its distal end contacts the selected point on vertebral body V. Biopsy needle 700 may be inserted in a known manner, such as percutaneously under fluoroscopic imaging, or under optical or magnetic image guidance (such as the STEALTH® system available from Medtronic Sofamor Danek). A small puncture in the vertebral body V is made using sharpened distal tip 708 (FIG. 9).

After pin 706 is removed from biopsy needle 700, guidewire 1 is inserted through biopsy needle 700 and affixed to vertebral body V. Guidewire I now is in position to direct further instruments and devices to the selected location on vertebral body V. Alternately, guidewire 1 may be inserted into vertebral body V without first using biopsy needle 700. The size of the working area may be increased at the physician's discretion. In instances where it is desired to increase the working area, the physician may use scalpel 800 along guidewire I (FIG. 15) to dissect additional tissue. In order to permit inspection of the position of guidewire 1 prior to insertion of a spine screw, a dilator 900 and optional retractor 10 may be inserted over the guidewire by inserting guidewire 1 through dilator opening 904 (FIG. 10B) with the dilator inserted through retractor 10. Once the dilator tip with retractor is inserted to the target site, the dilator may be removed and placement of the guidewire may be inspected through the retractor. If the surgeon is satisfied with the placement of guidewire 1, then the procedure may continue through the retractor or the retractor may be removed and another inserted with a screw. If, on the other hand, the surgeon desires to change the guidewire location, another guidewire may be placed through the retractor, such as by inserting bone biopsy needle 700 through the retractor to a different placement in the bone and inserting a new guidewire at the new location. The former guidewire may then be removed. If desired, the physician may pre-drill a threaded bore in vertebral body V using bone tap 140 (FIG. 11A) inserted along guidewire 1 to prepare the bore.

Referring now to FIGS. 16-21, embodiments of the presently disclosed minimally invasive retractor assemblies 100, 200, 300, 300A, 400, 400A, 500, and 600 will now be described.

Figure 16:
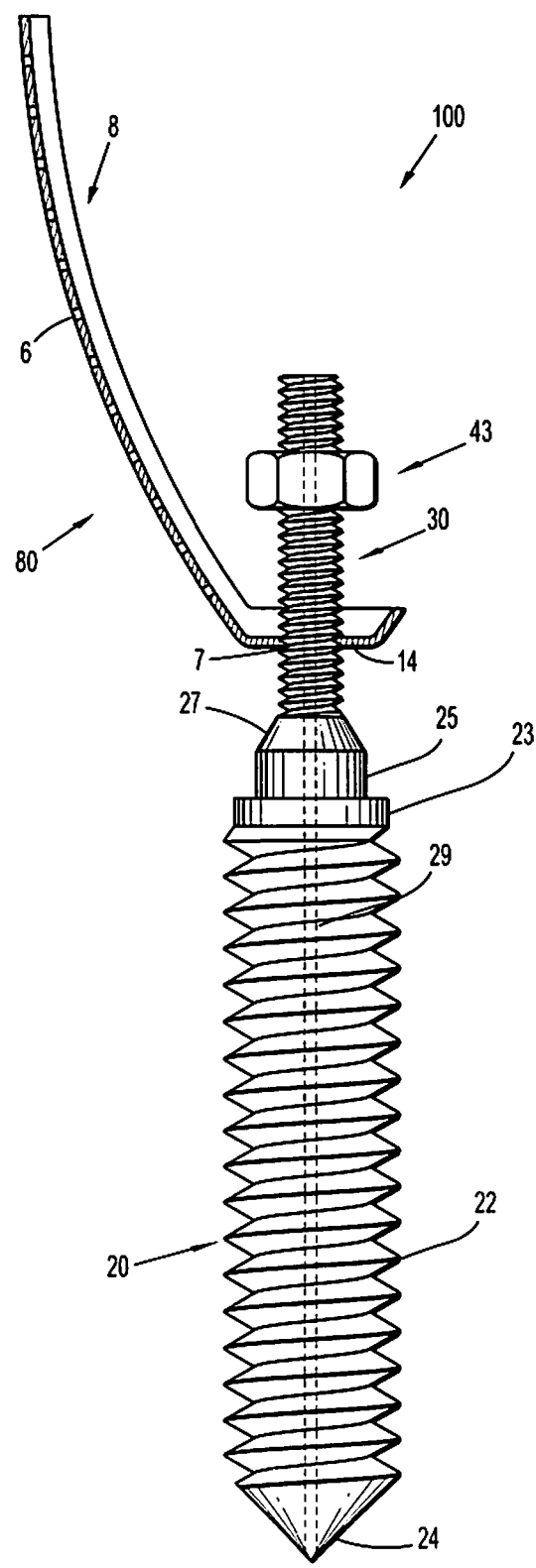
FIG. 16 is a side view of a minimally invasive retractor assembly including the the minimally invasive retractor of FIG. 8.

As shown in FIG. 16, minimally invasive retractor assembly 100 includes minimally invasive retractor 80, as described above with respect to FIG. 8 and a first embodiment of a posted screw 20. Posted screw 20 includes a threaded shank 22, a distal tip 24, and a collar 23. Threaded shank 22 is configured for engaging bone. A transition member 25 extends proximally from collar 23. Transition member 25 includes a tapered region 27. A threaded post 30 extends proximally from tapered region 27. It is contemplated that threaded post 30 may extend directly from collar 23, omitting transition member 25 and tapered region 27.

Alternatively, threaded post 30 may extend from transition member 25 with tapered region 27 omitted. A nut 43 has complementary threads to the threads on threaded post 30 for threadably engaging threaded post 30. Rotation of nut 43 in a first direction relative to threaded post 30 transitions nut 43 along threaded post 30 towards distal tip 24 of posted screw 20, while rotation of nut 43 in a second direction, opposite to the first direction, transitions nut 43 along threaded post 30 towards the proximal end of threaded post 30.

Although minimally invasive retractor assembly 100 is shown with a single retractor 80, it is contemplated that multiple retractors 80 may be used with a single posted screw 20. It is further contemplated that any of the presently disclosed embodiments of the minimally invasive retractor 10, 15, 50, 60, 70, or 80 may be used with posted screw 20. For example, as shown in FIG. 5, threaded post 30 of posted screw 20 is inserted through opening 7 of minimally invasive retractor 50.

In embodiments where multiple minimally invasive retractors 80 are used, each minimally invasive retractor 80 is positioned on the threaded post of posted screw 20 as discussed above, and held to the threaded post 30 by nut 43. Such an arrangement gives the surgeon a high degree of flexibility as to how to orient each retractor blade around the threaded post. Distal movement of minimally invasive retractor 80 is inhibited by tapered region 27, transition member 25, or collar 23 depending on which embodiment of posted screw 20 is used. Nut 43 is rotated in a first direction until minimally invasive retractor(s) 80 is (are) securely coupled to posted screw 20.

Alternatively, a single retractor having multiple retractor blades, such as retractor 70, could be mounted to the screw 20. For example, the threaded post 30 of screw 20 may extend through opening 7 of the retractor 70, with the retractor held in place on the screw by nut 43 or another capture mechanism, thereby providing a retractor having a plurality of arms extending from the screw 20.

Use of minimally invasive retractor assembly 100 will now be described. Retractor 80 is assembled with posted screw 20 as discussed above. The assembled apparatus is inserted into an incision through the patient's skin and muscle/fat tissue such that posted screw 20 may be threaded into bone such as a spinal pedicle or vertebral body. Once the screw is affixed to the bone, retractor blades 8 are spread apart to retract skin and tissue to create a retracted area at the target site. It is contemplated that at some locations a single retractor 80 may be used with a posted screw while other locations may have multiple retractors 80 coupled to a single posted screw. It is also contemplated that in embodiments, retractors having different numbers of blades may be coupled at different locations along the spine, i.e., retractors having different numbers of blades may be coupled to different vertebrae. For example, a retractor having a single blade may be coupled to a first vertebra, while a retractor having two or more blades may be coupled to a second vertebra. Various combinations of single and multiple retractors 80 may be used by the practitioner as desired for a particular procedure. In embodiments, posted screw 20 may be cannulated and include a channel 29 extending longitudinally through the posted screw 20.

The retractor blades 8 may be spread apart using Gelpi retractor 180 (FIG. 12) or by the physician manually grasping retractor blades 8 to urge them apart. With the retractor 80 spread apart the surgeon can inspect the surgical site, perform surgery on structures accessible through the retractor, and assemble other components to the threaded post, such as rod receiving connectors, links, etc. After the desired surgical steps have been performed, minimally invasive retractors 80 are removed.

One technique for removing retractors 80 includes rotating nut 43 in a second direction and separating nut 43 from post 30. This allows the practitioner to lift retractors 80 from the work site. In this approach, a rod attaching structure (i.e. an offset rod holder) may be mounted over the threaded post 30 and used to secure the rod attaching structure using one or more nuts 43. Once the desired number of rod attaching structures, links, etc. is coupled to posted screws 20, the practitioner installs a rod or rods to form the screw-rod construct. As part of forming the screw-rod construct, the practitioner may tunnel the rod subcutaneously between adjacent posted screws or may selectively make an incision between adjacent posted screws 20, which allows the rod to be inserted through the incision to adjacent posted screws 20. It is also contemplated that the nut which holds the retractor(s) onto the threaded post may remain in the body as part of the construct, with additional structures and nuts added above it. In this case, the retractor(s) may break away from the screw under force, such as by breaking at a relief region R, optionally provided.

Figure 17:
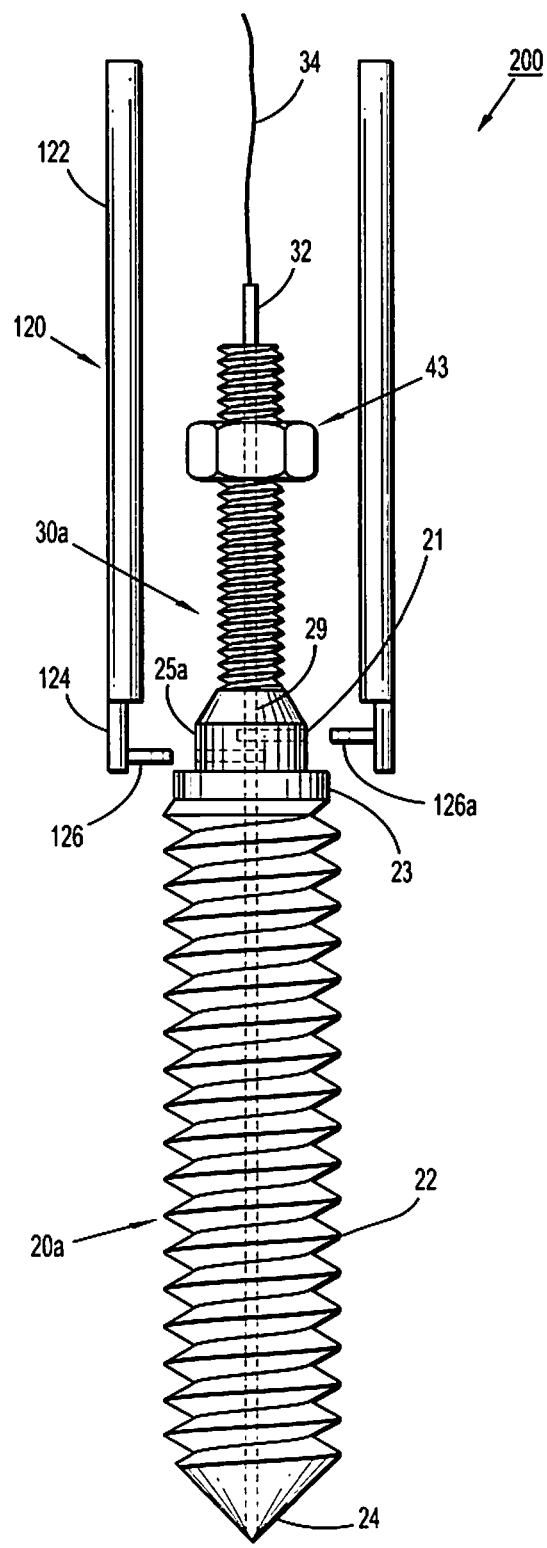
FIG. 17 is a side view of another embodiment of a minimally invasive retractor assembly.

With reference to FIG. 17, another embodiment of the minimally invasive retractor assembly or retractor assembly is shown generally as 200. Retractor assembly 200 includes a posted screw 20a and a pair of retractor blades 120. It is contemplated that only a single retractor blade 120 may be provided with posted screw 20a. Posted screw 20a includes a threaded shank 22, a distal tip 24, and a collar 23. Extending proximally from collar 23 is a threaded transition member 25a with a tapered region. A threaded post 30a extends proximally from the tapered region of transition member 25a. A nut 43 has complementary threads to the threads on post 30a for threadably engaging post 30a to attach structures to the threaded post 30a. Rotation of nut 43 in a first direction relative to post 30a transitions nut 43 towards distal tip 24 of posted screw 20a, while rotation of nut 43 in a second direction, opposite to the first direction, transitions nut 43 towards the proximal end of post 30a.

Channel 29 extends longitudinally through the screw 20a. Moreover, the channel 29 has an open end at the proximal end of threaded post 30a for receiving a pin 32 that is coupled to a wire 34. Although channel 29 is illustrated as extending fully through the screw 20a, in other embodiments, the channel 29 may partially extend through the screw 20a. For example, in an embodiment, the channel 29 may extend only through the post 30a and through the transition member 25a.

Moreover, while the pin 32 is shown as providing a locking mechanism for the blades 120 with respect to the transition member 25a, the blades 120 may be frictionally secured to the transition member 25a through the frictional engagement of the fingers 126 with the lumens 25a. In an embodiment, the guide wire 1 may extend through the length of the screw 20a and through the lumens 126a of fingers 126 of the blades 120, thereby inhibiting disengagement of the blades 120 from the transition member 25a during retraction. Once the desired procedure is complete, the guide wire 1 may be withdrawn and the blades 120 may then be disengaged from the transition member 25a.

Furthermore, transition member 25a includes opposing lumens 21 that are axially spaced apart. Each lumen 21 has an open end on the surface of transition member 25a and a closed end internal to transition member 25a. Each lumen 21 also intersects channel 29, although at two different locations along a longitudinal axis of transition member 25a. Each retractor blade 120 has a proximal portion 122 and a distal portion. A finger 126 extends substantially orthogonal to retractor blade 120. Finger 126 includes an opening 126a extending therethrough for slidably receiving pin 32 as will be described below. Each finger 126 is positionable within a lumen 21. When retractor blade 120 is coupled to posted screw 20, finger 126 is disposed within lumen 21 and pin 32 is seated in channel 29 such that pin 32 is engaged with the opening 126a of finger 126. When two retractor blades 120 are used, the respective fingers 126 are positioned within the respective lumens 21 and pin 32 engages both openings 126a of fingers 126, thereby releasably coupling retractor blades 120 to posted screw 20a. Proximal movement of wire 34 causes proximal translation of pin 32 through channel 29. Once pin 32 is separated from the openings 126a in fingers 126, retractor blades 120 may be separated from posted screw 20a and may be removed. An example of this type of retractor is disclosed in U.S. Patent Application Publication No. 2009/0222046, filed as U.S. application Ser. No. 12/396,188 on Mar. 2, 2009, the entire contents of which are hereby incorporated by reference herein.

Retractor assembly 200 is used in a similar manner as retractor assembly 100. With retractors 120 in place, tissue is retracted so the surgeon can inspect and perform surgery on accessible tissue and introduce additional components such as rod receiving links to be mounted to threaded post 30 and held in place by nut 43. Once retraction is no longer required, retractor blades 120 are removed by pulling on wire 34 such that pin 32 translates proximally and separates from fingers 126. Thus, retractor blades 120 may be removed from the working space. It is contemplated that single and double bladed retractor assemblies 200 may be used together and at various locations during the procedure.

Figure 18:
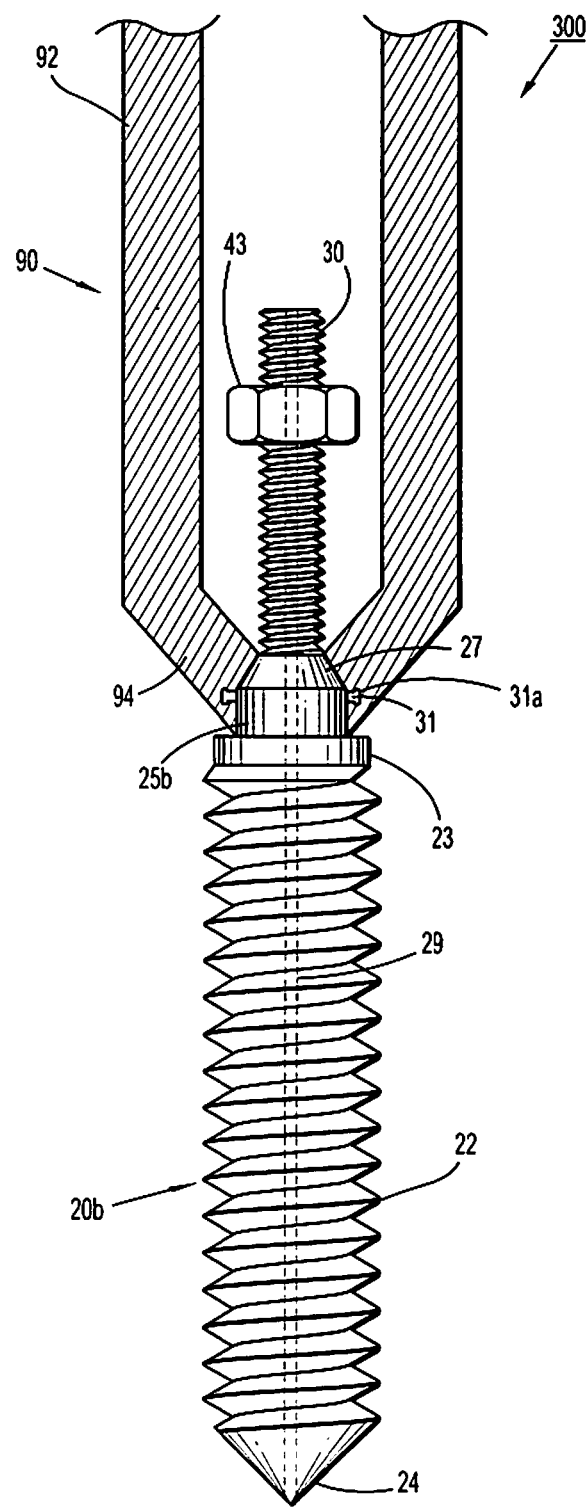
FIG. 18 is a side view of yet another embodiment of a minimally invasive retractor assembly.

In FIG. 18, retractor assembly 300 includes a posted screw 20b and one or more retractor blades 90. Posted screw 20b includes a threaded shank 22, a distal tip 24, and a collar 23. A transition member 25b extends proximally from collar 23 has a tapered region 27. A threaded post 30 includes external threads and extends proximally from tapered region 27. Posted screw 20b cannulated and includes a channel 29 extending longitudinally through the posted screw 20b.

It is contemplated that threaded post 30 may extend directly from collar 23, omitting transition member 25b and tapered region 27 of transition member 25b. In an embodiment, the transition member 25b may be generally cylindrical and the tapered region 27 of the transition member 25b would be omitted. Nut 43 has complementary threads to the threads on post 30 for threadably engaging post 30. Rotation of nut 43 in a first direction relative to post 30 transitions nut 43 towards distal tip 24 of posted screw 20b, while rotation of nut 43 in a second direction, opposite to the first direction, transitions nut 43 towards the proximal end of post 30.

To facilitate securing retractor blades 90 to the posted screw 20b, a pair of opposing protrusions 31 is arranged on an outer surface of transition member 25b. Although a pair of protrusions 31 is shown, it is contemplated that only one protrusion 31 or a plurality or multiplicity of protrusions may be positioned on transition member 25b. Furthermore, although protrusions 31 are shown perpendicular to a longitudinal axis of posted screw 20b, other angular arrangements are contemplated. Each retractor blade 90 includes a proximal portion and a distal portion 94. Distal portion 94 of each retractor blade 90 includes a recess 31a corresponding to protrusion 31 such that, when retractor blade 90 is coupled to posted screw 20b, the recess and protrusion 31 define a press-fit arrangement.

Alternatively, protrusion 31 may have specific surface characteristics (e.g. bulbous end) that correspond to surface characteristics of retractor blade 90 with retractor blade 90 over molded onto posted screw 20b and further secured to the screw by being molded around protrusion 31. An example of over molding a retractor blade to a screw is disclosed in U.S. Patent Application Publication No. 2009/0222045, filed as U.S. patent application Ser. No. 12/396,052 on Mar. 2, 2009, the entire contents of which are hereby incorporated by reference herein.

Figure 18A:
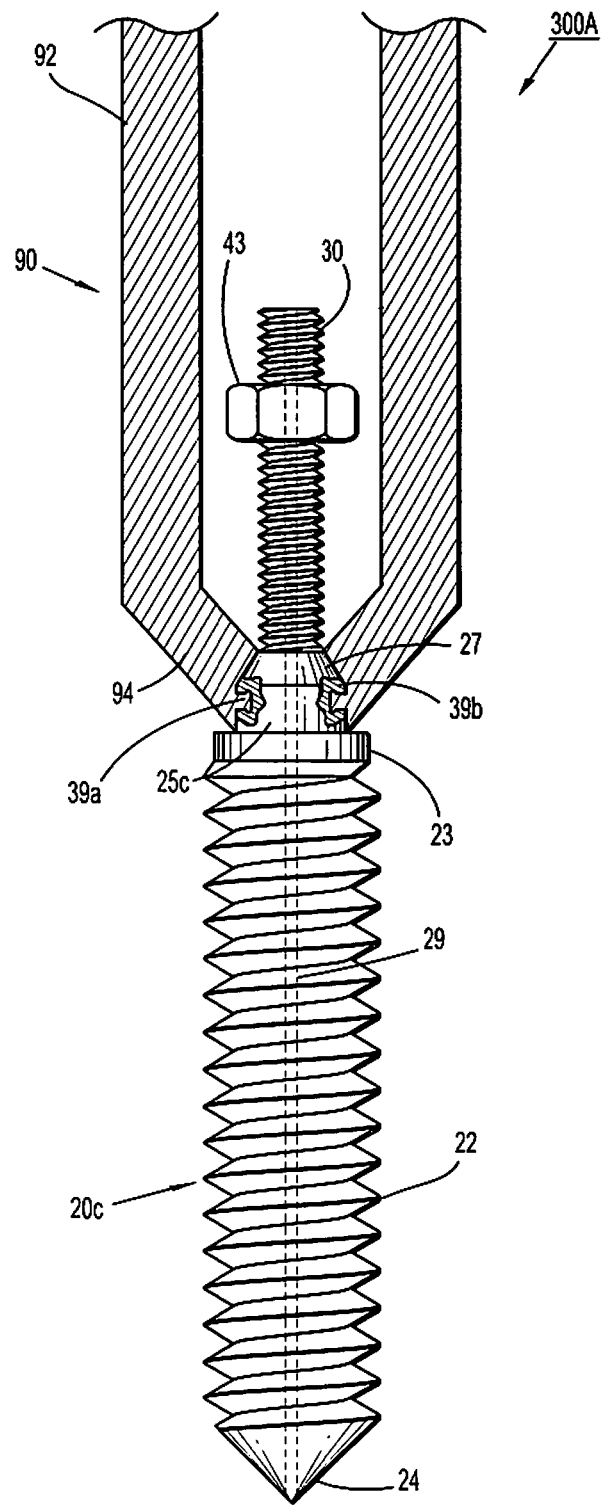
FIG. 18A is a side view of a further embodiment of a minimally invasive retractor assembly.

FIG. 18A depicts a retractor assembly 300A that is substantially similar to retractor assembly 300 except in the following respects. The retractor assembly 300A includes a protrusion 39a that is configured to engage a groove 39b to secure the retractor 90 to a transition member 25c. Posted screw 20c is cannulated and includes a channel 29 extending longitudinally through the posted screw 20b.

A further example of an over molded retractor is disclosed in U.S. Patent Application Publication No. 2009/0222044, filed as U.S. patent application Ser. No. 12/395,970 on Mar. 2, 2009, the entire contents of which are hereby incorporated by reference herein.

Figure 19:
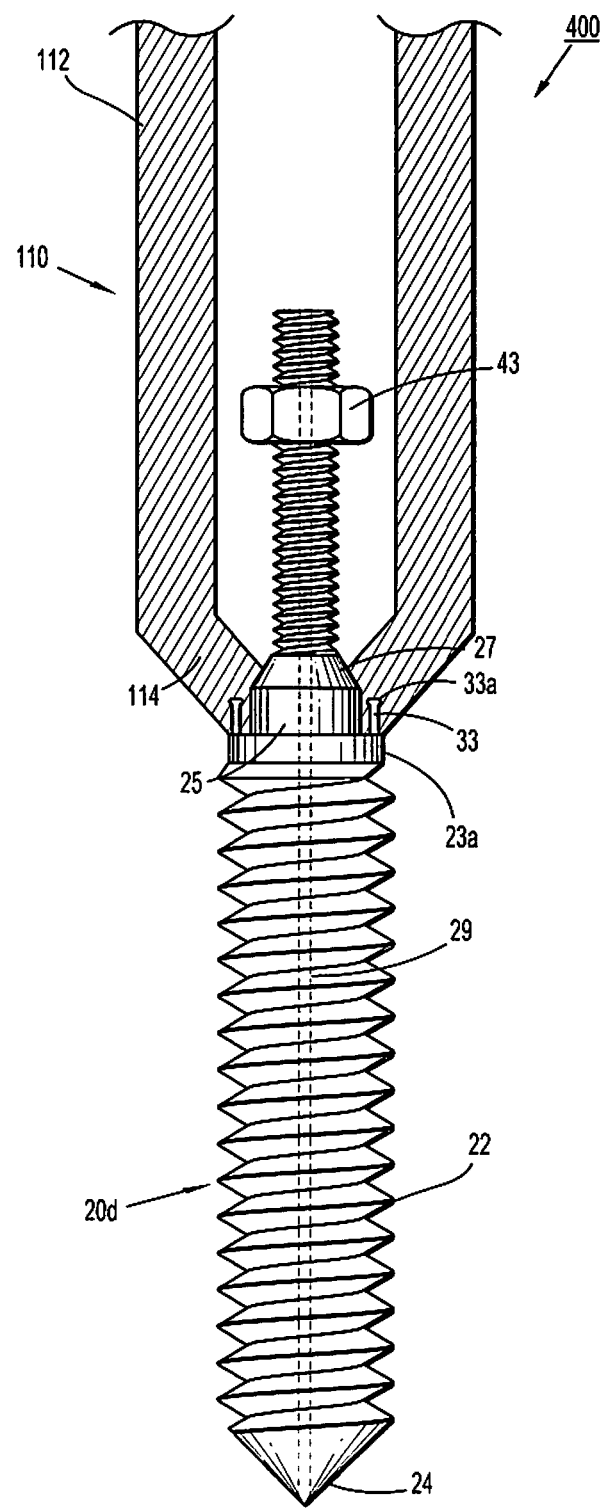
FIG. 19 is a side view of a still further embodiment of a minimally invasive retractor assembly.

Referring now to FIG. 19, retractor assembly 400 is illustrated. Retractor assembly 400 is substantially similar to retractor assembly 300 with the differences noted below. Retractor assembly 400 includes retractor blades 110 and posted screw 20d. Posted screw 20d is substantially similar to posted screw 20d, except that protrusions 33 extend proximally from collar 23a. Each retractor blade 110 includes a proximal region 112 and a distal region 114. Distal region 114 includes a recess 33a that cooperates with protrusion 33 to secure retractor blade 110 to posted screw 20d. As with retractor assembly 300, protrusions 33 and recesses cooperate for releasably attaching retractor blades 110 to posted screw 20d. Protrusions 33 and recesses may have complementary surface configurations similar to those of retractor assembly 300 and may be over molded as previously disclosed.

Figure 19A:
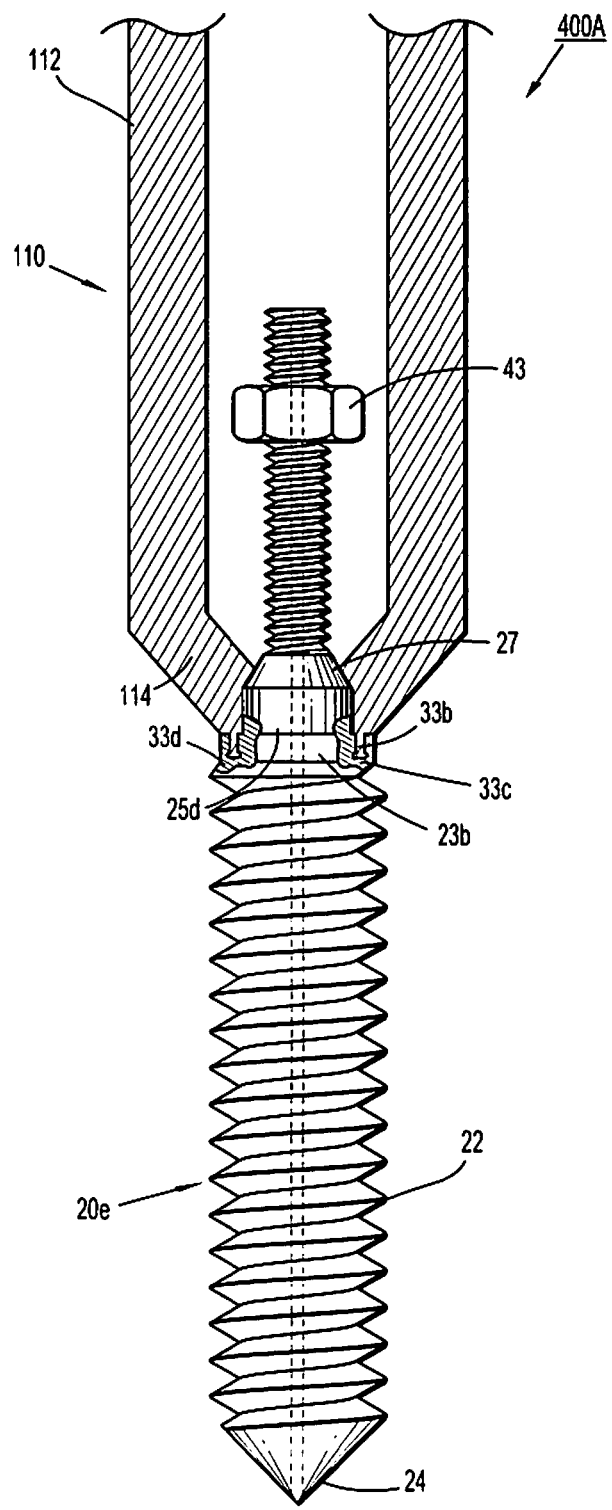
FIG. 19A is a side view of yet a further embodiment of a minimally invasive retractor assembly.

As shown in FIG. 19A, a retractor assembly 400A is substantially similar to retractor assembly 400 except that retractor blades 110 include protrusions 33b that engage grooves 33c within collar 23a to secure the retractor blades 110 to the screw 20e. As shown in FIG. 23A, the collar 23b and the transition member 25d may include a retaining member 33d that includes the groove 33c that engages the protrusion 33b to secure the retractor blades 110 to the screw 20e Retractors 300, 300A, 400 and 400A are used similarly, with the only distinction being the points of attachment between retractor blades 90, 110 and posted screws 20b-e. Furthermore, retractors 300-400A are used similarly to retractor 100 and the procedure will not be repeated for the sake of brevity. To remove retractors 300, 300A, 400, 400A when they are no longer needed, each retractor is pulled away from the screw to which is operably coupled such that the frictional engagement of the retractor with features, e.g., protrusions 31, 39a, 33, 33b, is overcome, or the retractor breaks away from features, e.g., protrusions 31, 39a, 33, 33b, if molded over those features.

Figure 20:
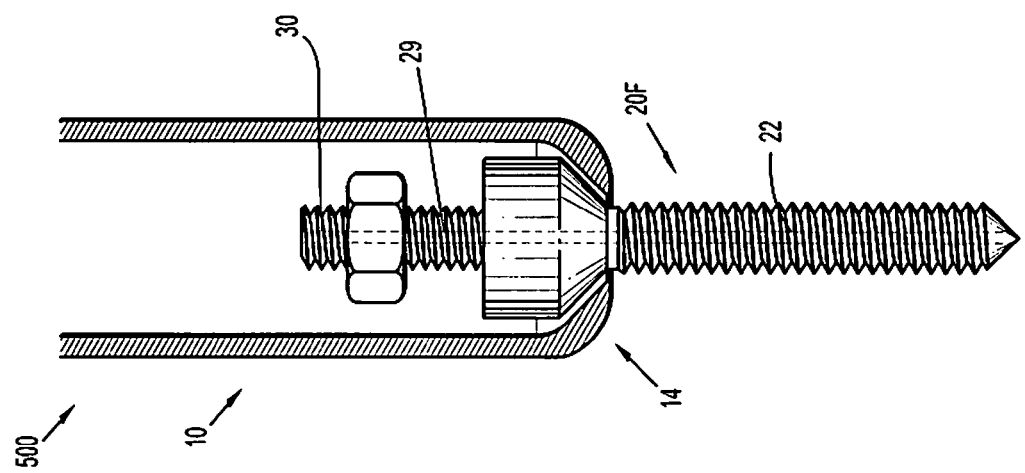
FIG. 20 is a cross-sectional view of a minimally invasive retractor assembly including the minimally invasive retractor of FIG. 1.

Referring now to FIG. 20, a retractor assembly 500 will now be described. Retractor assembly includes a posted screw may be provided which includes a threaded shank 22, a transition member 28a, and a threaded post 30 extending proximally from the transition member 28a. FIG. 20 is a cross-section view illustrating a retractor of the type shown in FIGS. 1-4 mounted with the threaded shank 22 extending through aperture 7 of the retractor 10. As shown in FIG. 20, the transition member 28a has a radial dimension that permits the distal end 14 of the retractor 10 to receive and support the transition member 28a without permitting the screw 20d to pass through aperture 7. The radial dimension of the transition member 28a may change along the longitudinal axis of the screw 20f, e.g., the transition member 28a may have a substantially parabolic configuration. In this configuration, the screw 20d and the retractor 10 are inserted into the surgical site, the threaded shank 22 is screwed into bone, and the retractor 10 is used by spreading the retractor blades 8 to provide visibility and access to the surgical site. Once retraction is no longer required, the retractor 10 is pulled over the screw 20f, such that the retractor 10 flexes or breaks at the relief region(s) R to permit the retractor 10 to be separated from the screw 20f.

Figure 21:
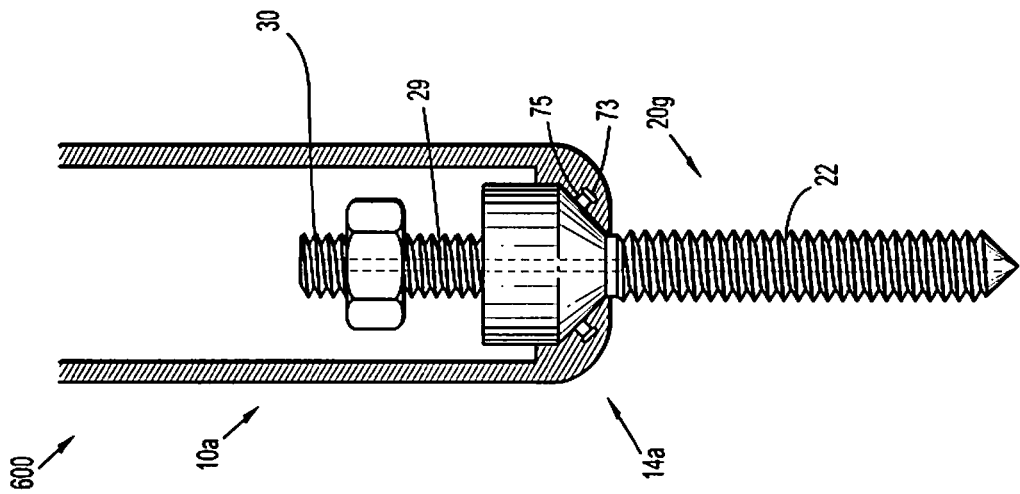
FIG. 21 is a cross-sectional view of yet another embodiment of a minimally invasive retractor assembly.
Figure 24:
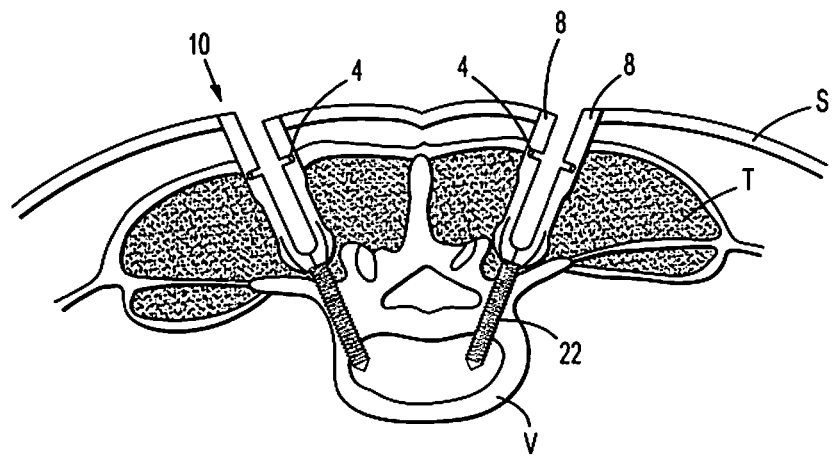
FIG. 24 is a front cross sectional view of a body with the minimally invasive retractor assembly of FIG. 22 attached to the body and shown flush with the skin of the body.

FIG. 21 shows a retractor assembly 600 having construction similar to that shown in FIG. 24, except that the retractor 10a is over-molded onto the screw 20g. In this configuration, the retractor 10a is molded to surround the base of transition member 28b. To facilitate a secured relation between the screw 20g and the retractor 10a, one or more protrusions 26a operatively coupled to the transition member 28b have a corresponding shape to one or grooves 26b within distal end 14a of the retractor 10a. Alternatively, the retractor 10a may include protrusions 73 that engage grooves 75 defined within the transition member 28b. As with the embodiment of FIG. 20, the screw 20g and retractor 10a are inserted to the surgical site, the threaded shank 22 is screwed into bone, and the retractor 10a is used by spreading the retractor blades to provide visibility and access to the site. Once retraction is no longer required, the retractor 10a is pulled over the screw 20g, such that the retractor flexes or breaks at the relief region(s) to permit the retractor to be separated from the screw 20g.

Figure 22:
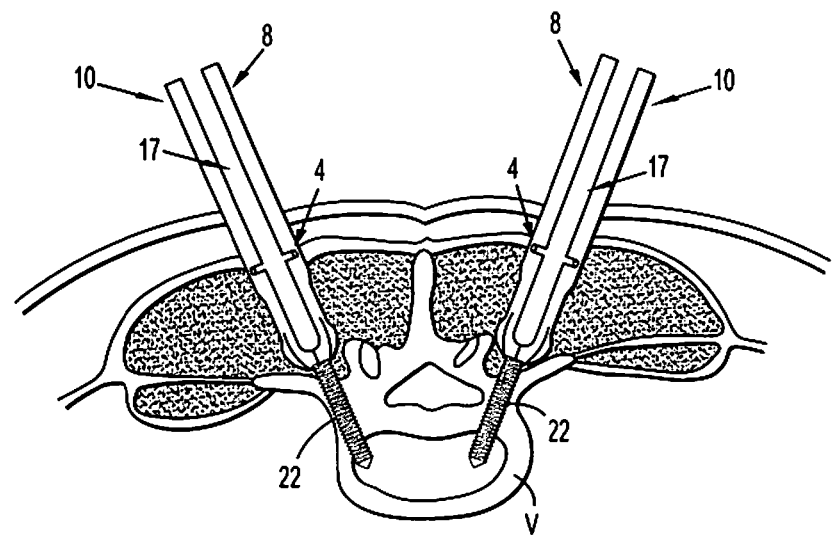
FIG. 22 is a front cross-sectional view of a body with a minimally invasive retractor assembly including the retractor of FIG. 1 attached to the body using screws with the blades in their initial position.
Figure 23:
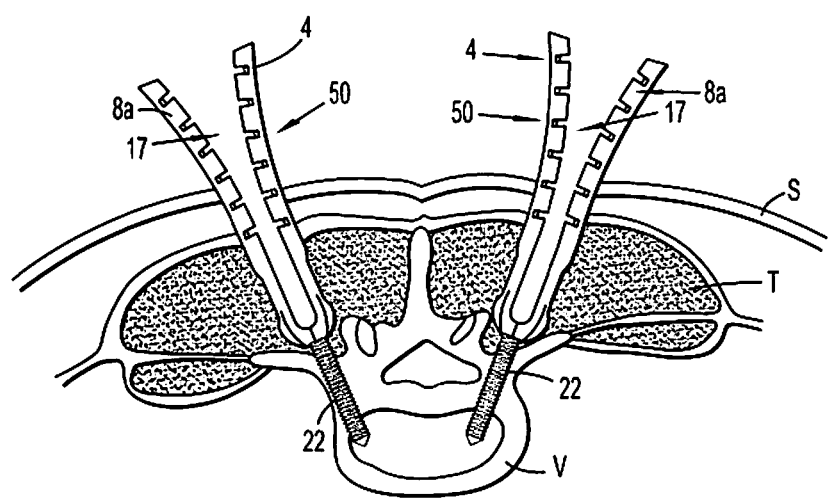
FIG. 23 is a front cross-sectional view of a body with another embodiment of a minimally invasive retractor assembly including the retractor of FIG. 5 attached to the body.
Figure 25:
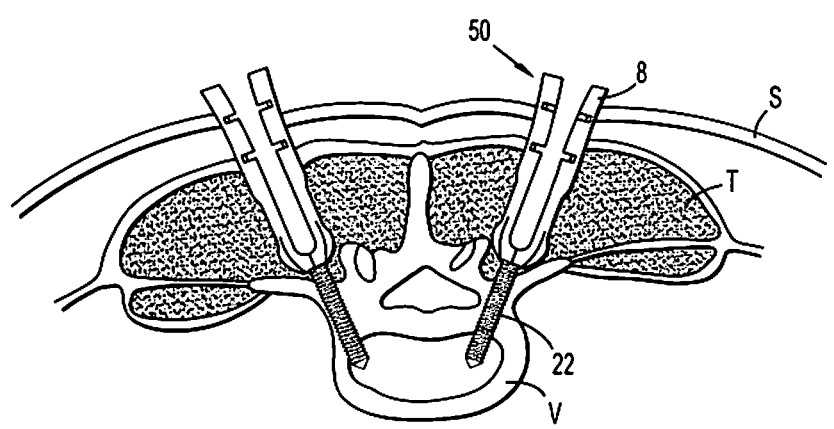
FIG. 25 is a front cross-sectional view of a body with the minimally invasive retractor assembly of FIG. 23 shown near the surface of the skin of the body.
Figure 28:
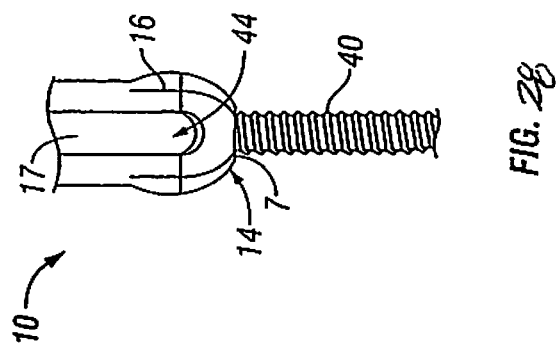
FIG. 28 is an enlarged side view of the detailed area "28" of FIG. 26.
Figure 27:
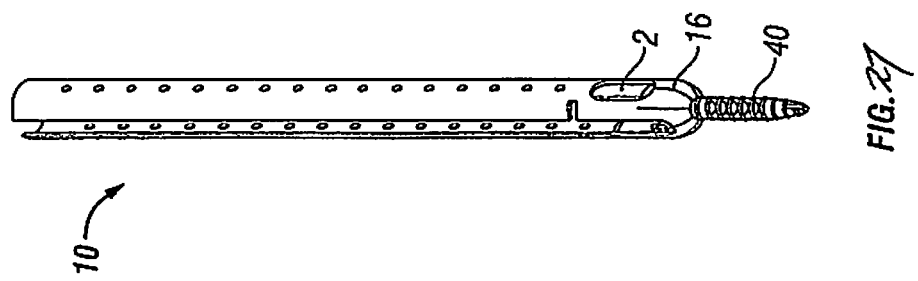
FIG. 27 is a perspective view of the minimally invasive retractor and screw assembly of FIG. 26.
Figure 26:
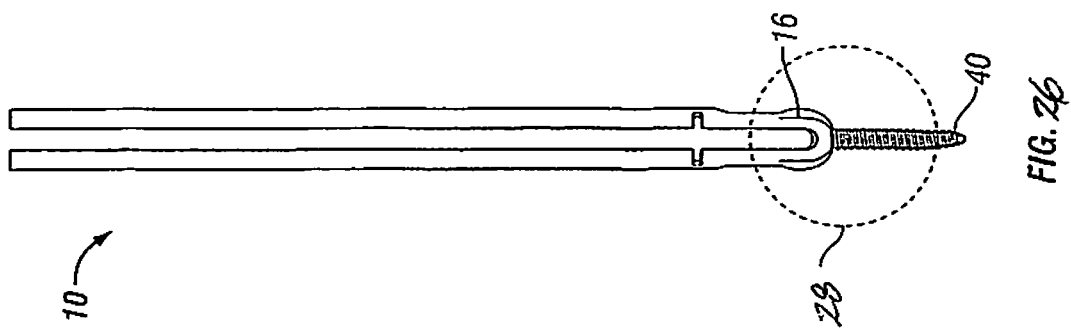
FIG. 26 is a side view of a minimally invasive retractor and screw assembly including the minimally invasive retractor of FIG. 1.
Figure 29:
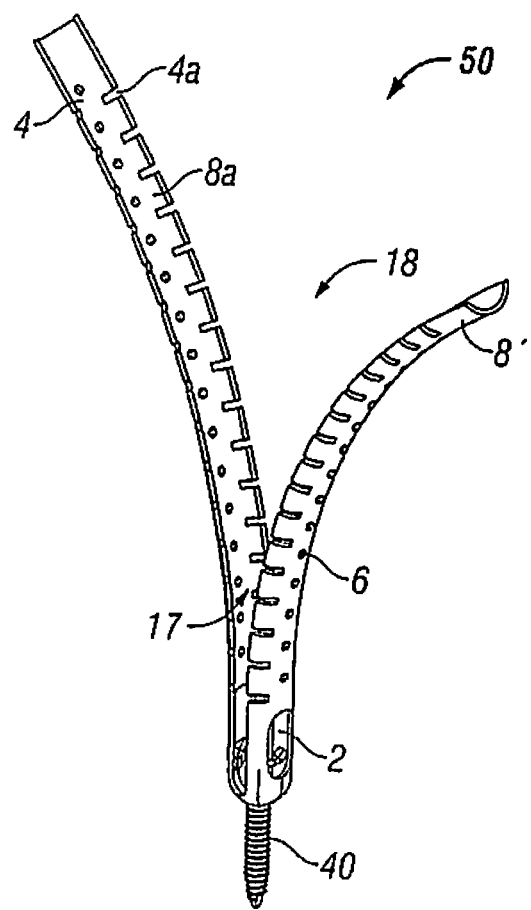
FIG. 29 is a perspective view of a minimally invasive retractor and screw assembly according to another embodiment of the present disclosure.

As shown in FIGS. 22 and 23, a retractor 10 may be assembled with screw 20. The assembled apparatus is inserted into an incision through the patient's skin S and muscle/fat tissue T such that screw 20 is subsequently threaded into a vertebral body V. Once the desired number of retractors 10 are affixed to vertebral body V, retractor blades 8 are spread apart to retract skin S and tissue T to create a retracted area at the target site. Alternatively, retractor 50 may be assembled with pedicle screw 20 retract the tissue as shown in FIG. 23. As shown in FIGS. 24 and 25, the retractors 10, 50 may be substantially flush with the surface of the skin S. The length of retractors 10, 50 may be adjusted, as desired, by cutting excess material using scissors or a knife. Although FIGS. 22-25 are illustrated with retractors 10, 50, other embodiments of retractors, such as the ones described above, may be used in the manner described with respect to FIGS. 22-25.

It will be understood that various modifications may be made to the embodiments of the presently disclosed retractors and posted screws. It should also be noted that the figures are not necessarily to scale. Therefore, the above description should not be construed as limiting, but merely as exemplifications of embodiments. Those skilled in the art will envision other modifications within the scope and spirit of the present disclosure.

For example, while the foregoing description has focused on spine surgery, it is contemplated that the retractors and methods described herein may find use in other orthopedic surgery applications, such as trauma surgery. Thus, where it is desired to insert a screw or pin into bone in a minimally invasive manner, or otherwise to access a surgical target site over a guidewire, the dilator, scalpel and retractors (or some of them) of the present disclosure may be used, with or without a bone screw.

What is claimed is:

1. A minimally invasive retractor assembly, comprising:
   at least one retractor including a pair of retractor blades;
   a posted screw defining a longitudinal axis, the screw including a post, a collar, a transition member interposed between the collar and the post, and a shank extending distally from the collar, the transition member tapered along the longitudinal axis, the shank insertable into bone, the transition member and the pair of retractor blades including complementary members that are engageable with one another to releasably secure the pair of retractor blades to the transition member, the posted screw defining a longitudinal channel extending through the shank; and
   a pin configured and dimensioned to be received within the longitudinal channel, wherein the complementary members of the posted screw and the pair of retractor blades are operatively associated with the longitudinal channel, whereby the pin inserted through the shank of the posted screw releasably secures the pair of retractor blades to the screw, the pair of retractor blades radially translatable relative to the longitudinal axis of the screw.

2. The minimally invasive retractor assembly of claim 1, wherein the retractor blades define a first state in which the retractor blades are substantially parallel to each other and a second state in which the retractor blades define a substantially V-shaped configuration.

3. The minimally invasive retractor assembly of claim 1, wherein the complementary members include a protrusion and a groove that are engageable with one another.

4. The minimally invasive retractor assembly of claim 1, wherein the pair of retractor blades includes protrusions and the transition member includes grooves, the protrusions receivable within the grooves, the longitudinal channel extending through the post and the transition member, the protrusions including longitudinally extending lumens, and the pin receivable within the longitudinal channel and through the longitudinally extending lumens when the protrusions of the pair of retractor blades are placed within the grooves of the transition member.

5. The minimally invasive retractor assembly of claim 4, further comprising a wire, the wire operably coupled to a proximal end of the pin, the wire translatable through the longitudinal channel.

6. The minimally invasive retractor assembly of claim 4, wherein the pair of retractor blades is overmolded over the transition member of the screw.

7. The minimally invasive retractor assembly of claim 1, wherein the transition member defines grooves configured to receive the respective complementary members of the pair of retractor blades.

8. The minimally invasive retractor assembly of claim 7, wherein the grooves of the transition member are in communication with the longitudinal channel.

9. The minimally invasive retractor assembly of claim 8, wherein the grooves of the transition member are substantially orthogonal to the longitudinal channel.

10. The minimally invasive retractor assembly of claim 8, wherein the complementary members of the pair of retractor blades each define a bore configured to be aligned with the longitudinal channel when the complementary members are disposed in the respective grooves of the transition member.

11. The minimally invasive retractor assembly of claim 1, wherein the complementary member of a first retractor blade of the pair of retractor blades is distal of the complementary member of a second retractor blade of the pair of retractor blades.

12. The minimally invasive retractor assembly of claim 1, wherein the retractor blades diametrically oppose each other.

13. The minimally invasive retractor assembly of claim 1, wherein the collar has a diameter larger than a diameter of the transition member.

* * * * *